(12) United States Patent
DiGrazia

(10) Patent No.: US 8,591,447 B2
(45) Date of Patent: Nov. 26, 2013

(54) WOUND AND BANDAGE PROTECTION SYSTEM AND METHOD

(76) Inventor: Jennifer DiGrazia, Brooklyn, NY (US)

( * ) Notice: Subject to any disclaimer, the term of this patent is extended or adjusted under 35 U.S.C. 154(b) by 297 days.

(21) Appl. No.: 12/826,644

(22) Filed: Jun. 29, 2010

(65) Prior Publication Data

US 2011/0319798 A1 Dec. 29, 2011

(51) Int. Cl.
*A61F 5/00* (2006.01)
*A61F 13/00* (2006.01)

(52) U.S. Cl.
USPC ......... 602/79; 602/3; 602/41; 602/42; 602/75

(58) Field of Classification Search
USPC .............. 602/41–59, 73–79, 3; D24/190–192
See application file for complete search history.

(56) References Cited

U.S. PATENT DOCUMENTS

| | | | |
|---|---|---|---|
| 679,918 A | 8/1901 | Shears | |
| 697,637 A | 4/1902 | Lee | |
| 1,610,089 A | 12/1926 | Heitler | |
| 2,233,209 A | * 2/1941 | Herzog | ............................ 602/58 |
| 2,273,873 A | 2/1942 | Klein | |
| 2,367,690 A | 1/1945 | Purdy | |
| 2,632,443 A | 3/1953 | Lesher | |
| 3,419,003 A | 12/1968 | Krauss et al. | |
| 3,504,672 A | 4/1970 | Moon | |
| 3,667,462 A | 6/1972 | Moon | |
| 3,954,105 A | 5/1976 | Nordby et al. | |
| 4,036,220 A | 7/1977 | Bellasalma | |
| 4,263,906 A | 4/1981 | Finley | |
| 4,399,816 A | 8/1983 | Spangler | |
| 4,641,643 A | 2/1987 | Greer | |
| 4,665,909 A | 5/1987 | Trainor | |
| 4,727,864 A | 3/1988 | Wiesenthal et al. | |
| 4,907,579 A | 3/1990 | Kum | |
| 4,909,243 A | 3/1990 | Frank et al. | |
| 4,911,151 A | 3/1990 | Rankin et al. | |

(Continued)

FOREIGN PATENT DOCUMENTS

| CH | 676197 A5 | 12/1990 |
|---|---|---|
| CN | 2538314 Y | 3/2003 |

(Continued)

OTHER PUBLICATIONS

Bowswear, LLC, Printed Jul. 18, 2013, Bowsewear,LLC announces "Healers Veterinary dressings"—a new class of products that changes the way pet lovers bandage and protect their pets injuries, http//sites.webed.me/healers/press-releases/bowsewearllc-announces-%E2%80%9Chealers-veterinary-dressings%E2%80%9D-%E2%80%93-a-new-class-of-products-that-changes-the-way-pet-lovers-bandage-and-protect-their-pets-injuries/ , 2 pages.

(Continued)

*Primary Examiner* — Kim M Lewis
(74) *Attorney, Agent, or Firm* — Office of M. Zev Levoritz; Menachem Zev Levoritz

(57) ABSTRACT

Wound/bandage protectors configured as a wrap, a sock/mitten, or a bandage, which may be made out of stretchable material. The wrap may have one or more fastening straps as well as possibly a first catch fastening surface. The sock/mitten may have a fastening strap and a sheath. The wrap, the sock/mitten, and the bandages may have apertures and aperture covers. In addition, the bandages may have diamond or triangular gauze configurations.

10 Claims, 27 Drawing Sheets

(56) References Cited

U.S. PATENT DOCUMENTS

| | | | |
|---|---|---|---|
| 4,911,156 A | 3/1990 | Libertucci |
| 5,086,763 A | 2/1992 | Hathman |
| 5,137,508 A | 8/1992 | Engman |
| 5,244,523 A | 9/1993 | Tollini |
| 5,342,286 A | 8/1994 | Kelly et al. |
| 5,354,261 A | 10/1994 | Clark et al. |
| 5,395,302 A | 3/1995 | Botha et al. |
| 5,449,340 A | 9/1995 | Tollini |
| 5,456,660 A | 10/1995 | Reich et al. |
| 5,495,828 A | 3/1996 | Solomon et al. |
| 5,538,500 A | 7/1996 | Peterson |
| 5,562,107 A | 10/1996 | Lavender et al. |
| 5,592,953 A | 1/1997 | Delao |
| 5,662,599 A | 9/1997 | Reich et al. |
| 5,702,356 A | 12/1997 | Hathman |
| 5,843,018 A | 12/1998 | Shesol et al. |
| 5,843,025 A | 12/1998 | Shaari |
| 5,897,519 A | 4/1999 | Shesol et al. |
| 5,918,599 A | 7/1999 | Shesol |
| 5,919,180 A | 7/1999 | Raimondo |
| 5,964,721 A | 10/1999 | Augustine |
| 5,994,613 A | 11/1999 | Cummings et al. |
| 6,000,366 A | 12/1999 | Reeping |
| 6,013,097 A | 1/2000 | Augustine et al. |
| 6,070,557 A | 6/2000 | Hibbert |
| 6,164,279 A | 12/2000 | Tweedle |
| 6,186,097 B1 | 2/2001 | Brockmann et al. |
| 6,255,552 B1 | 7/2001 | Cummings et al. |
| 6,257,240 B1 | 7/2001 | Shesol |
| 6,258,051 B1 * | 7/2001 | Shesol et al. ............... 602/79 |
| 6,274,787 B1 | 8/2001 | Downing |
| 6,293,917 B1 | 9/2001 | Augustine et al. |
| 6,307,118 B1 | 10/2001 | Reich |
| 6,512,159 B1 | 1/2003 | Shesol et al. |
| 6,526,920 B1 | 3/2003 | Griffin |
| 6,659,970 B1 * | 12/2003 | Woodworth et al. ......... 602/3 |
| 6,762,337 B2 | 7/2004 | Boukanov et al. |
| 6,894,204 B2 | 5/2005 | Dunshee |
| 7,118,545 B2 | 10/2006 | Boyde |
| 7,264,602 B1 | 9/2007 | Longsworth |
| D573,260 S | 7/2008 | Dunshee |
| 7,576,257 B2 | 8/2009 | La Greca, Sr. |
| 7,780,615 B1 | 8/2010 | Shesol |
| 2002/0115955 A1 | 8/2002 | DeSena |
| 2003/0036716 A1 | 2/2003 | Knutson et al. |
| 2003/0153861 A1 | 8/2003 | Royer |
| 2004/0133144 A1 | 7/2004 | Crichton |
| 2005/0010154 A1 | 1/2005 | Wright et al. |
| 2007/0010775 A1 | 1/2007 | Lutri |
| 2007/0033711 A1 | 2/2007 | Achtelstetter |
| 2007/0078364 A1 | 4/2007 | Davis Belcher |
| 2008/0015483 A1 | 1/2008 | Kilbey |
| 2008/0039760 A1 | 2/2008 | Lesko |
| 2008/0103451 A1 | 5/2008 | Schaefer, Jr. et al. |
| 2008/0127907 A1 | 6/2008 | Purtell et al. |
| 2008/0312572 A1 | 12/2008 | Riesinger |

FOREIGN PATENT DOCUMENTS

| | | |
|---|---|---|
| DE | 10231701 A1 | 2/2004 |
| FR | 2843539 A1 | 2/2004 |
| GB | 319215 A | 12/1930 |
| GB | 2358141 A | 7/2001 |
| JP | 11216158 A | 8/1999 |
| NZ | 280249 | 10/1997 |
| WO | 9406382 A1 | 3/1994 |
| WO | 9500087 A1 | 1/1995 |
| WO | 0238096 A2 | 5/2002 |
| WO | 2006053222 A2 | 5/2006 |
| WO | 2010015227 A2 | 2/2010 |

OTHER PUBLICATIONS

Amazon.com, Inc, Printed Jul. 18, 2013, HEALERS Medical Dog Boots and Gauze Pads, Blue, http://www.amazon.com/HEALERS-Medical-Dog-Boots-Bandages/dp/B006GKJ4D2/ref=sr_1_3?s=pet-supplies&ie=UTF8&qid=1373028156, 1 page.

PCT International Search Report and Written Opinion of the International Searching Authority for PCT Application PCT/US2011/042216, Mailing Date- Apr. 6, 2012, 18 pages.

* cited by examiner

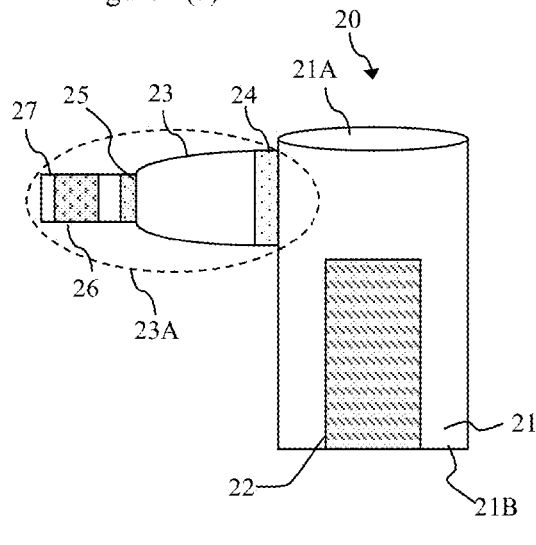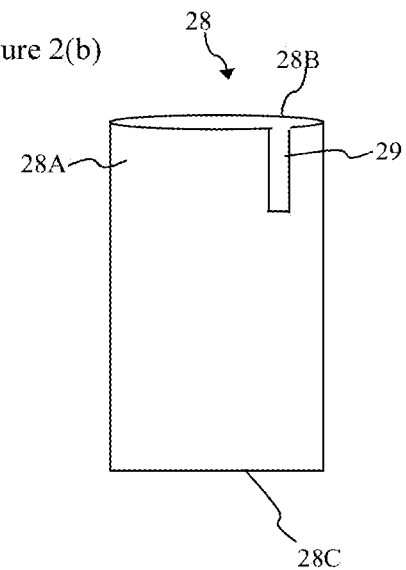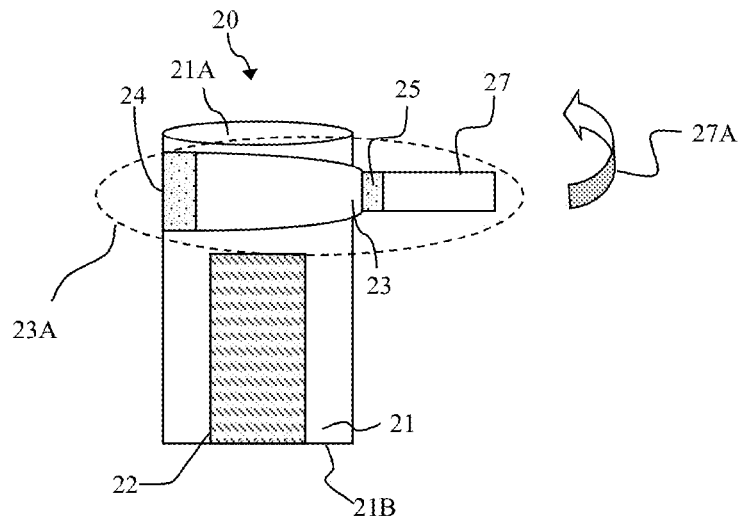

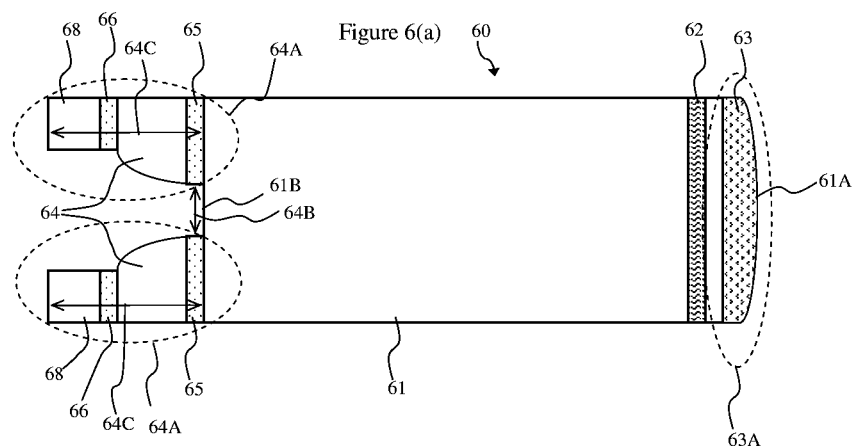
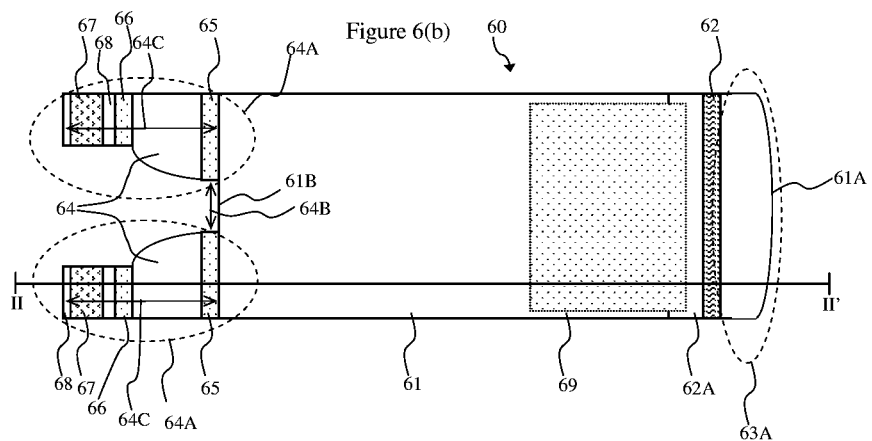
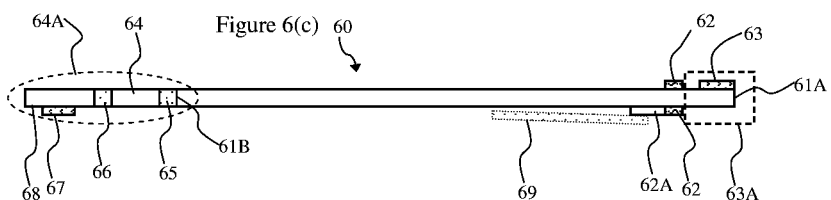

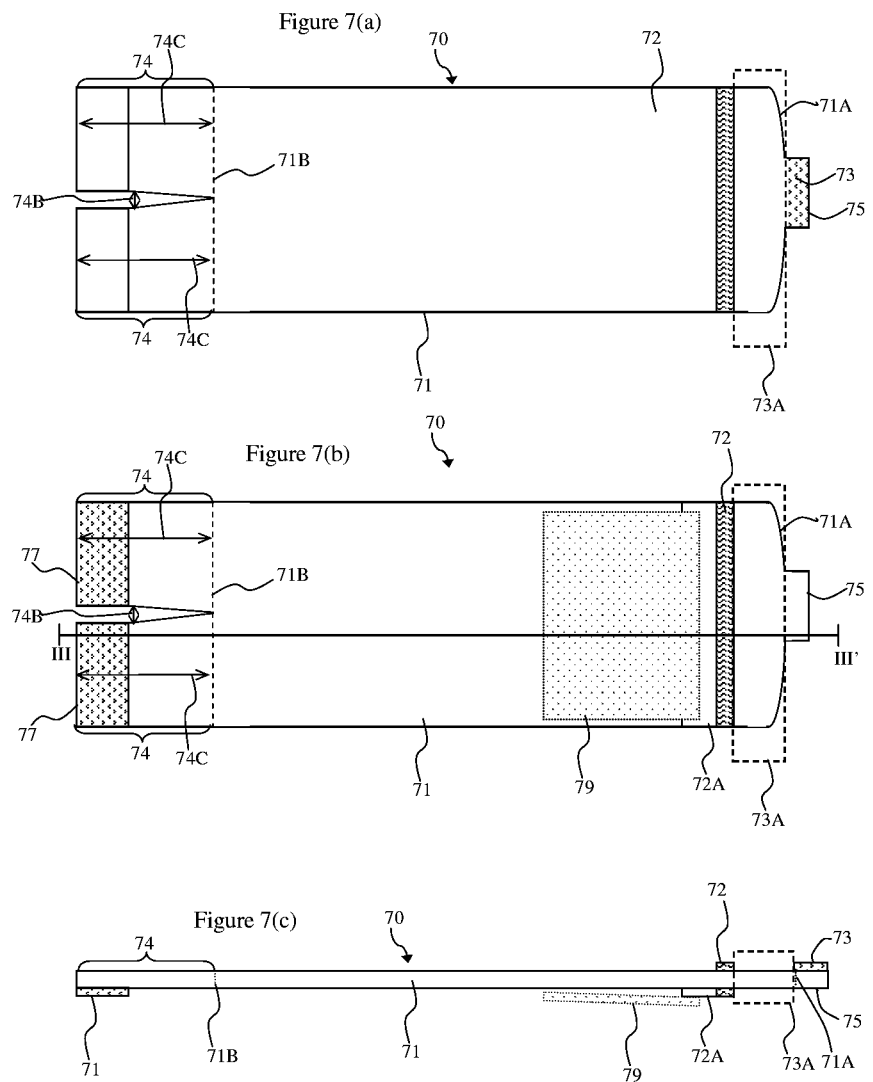

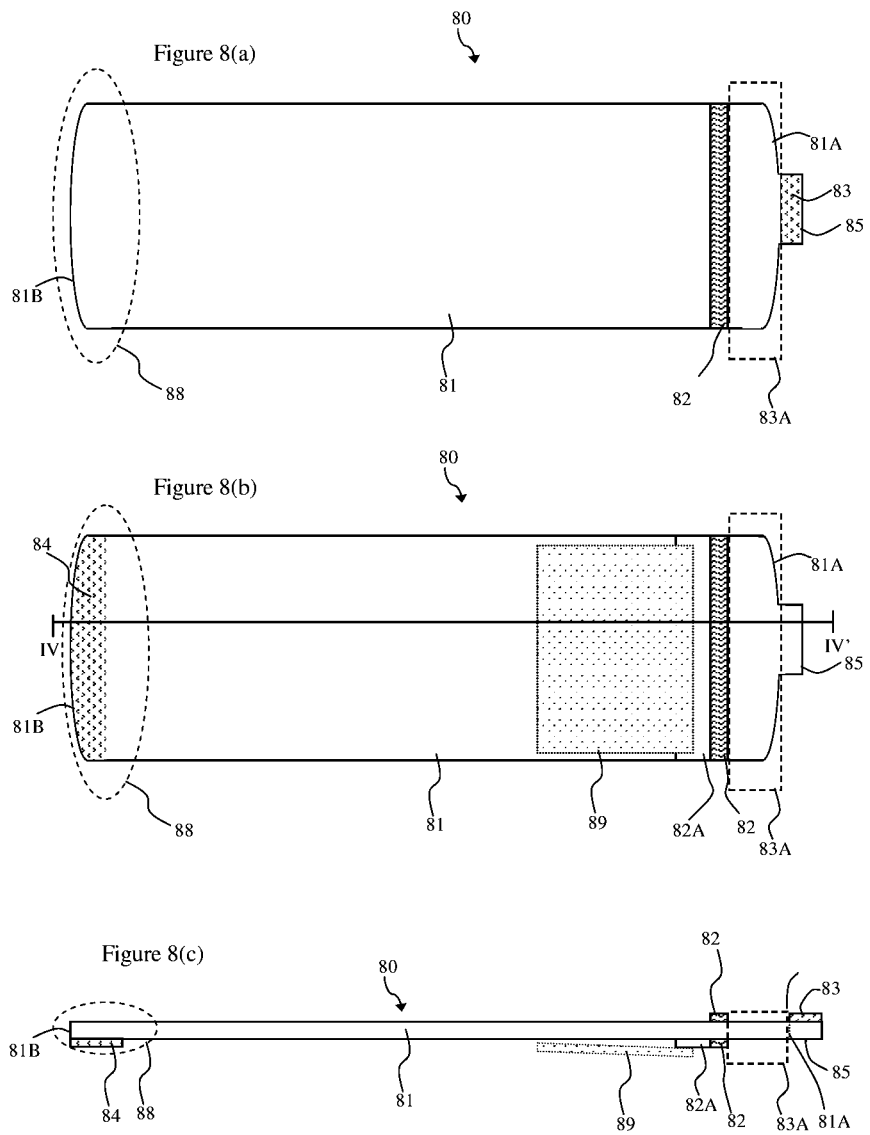

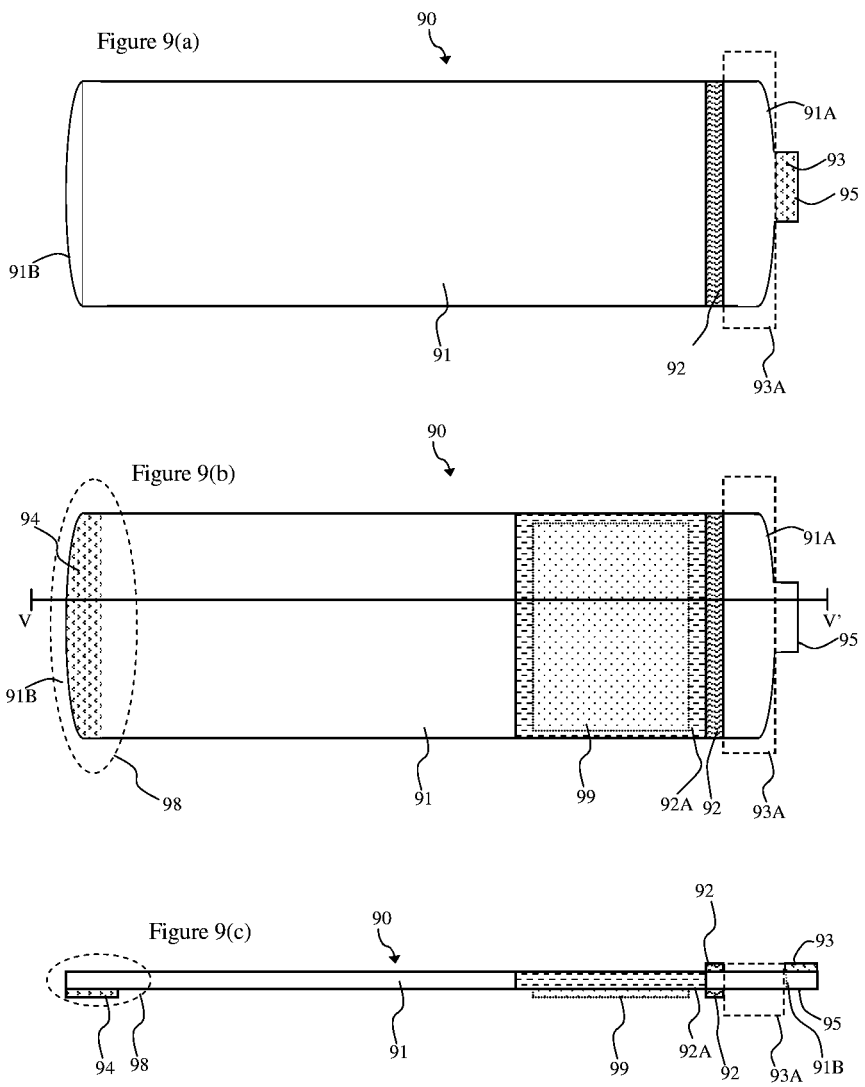

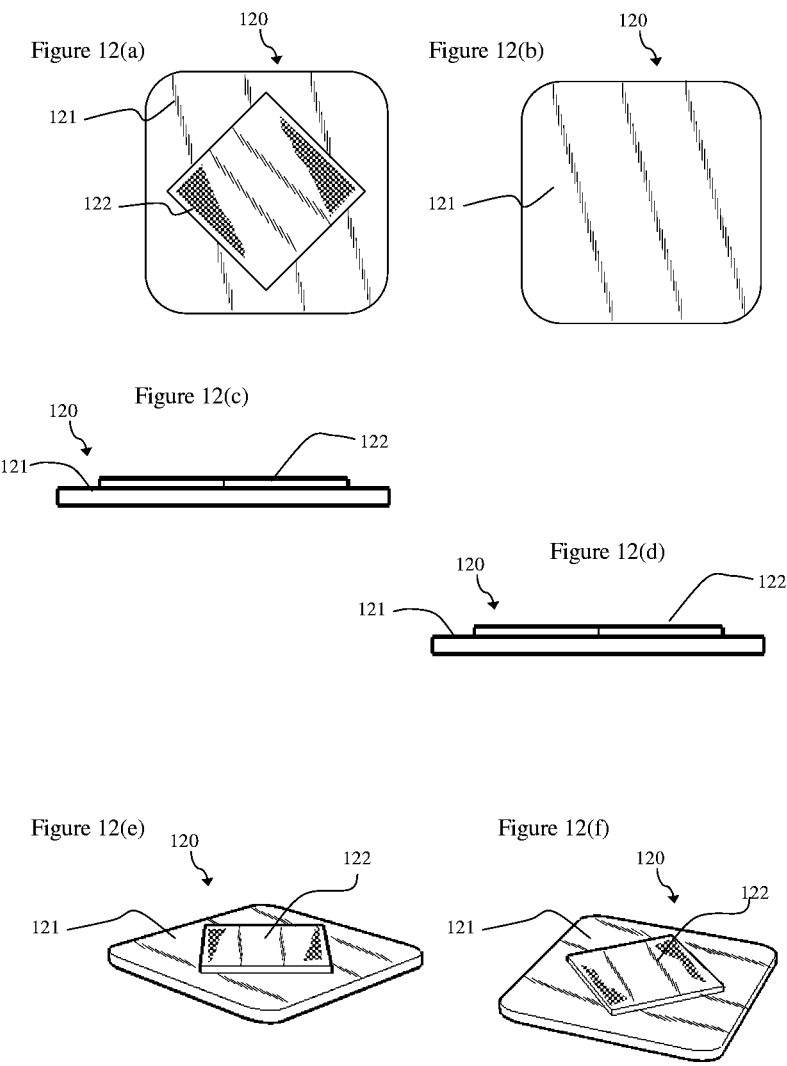

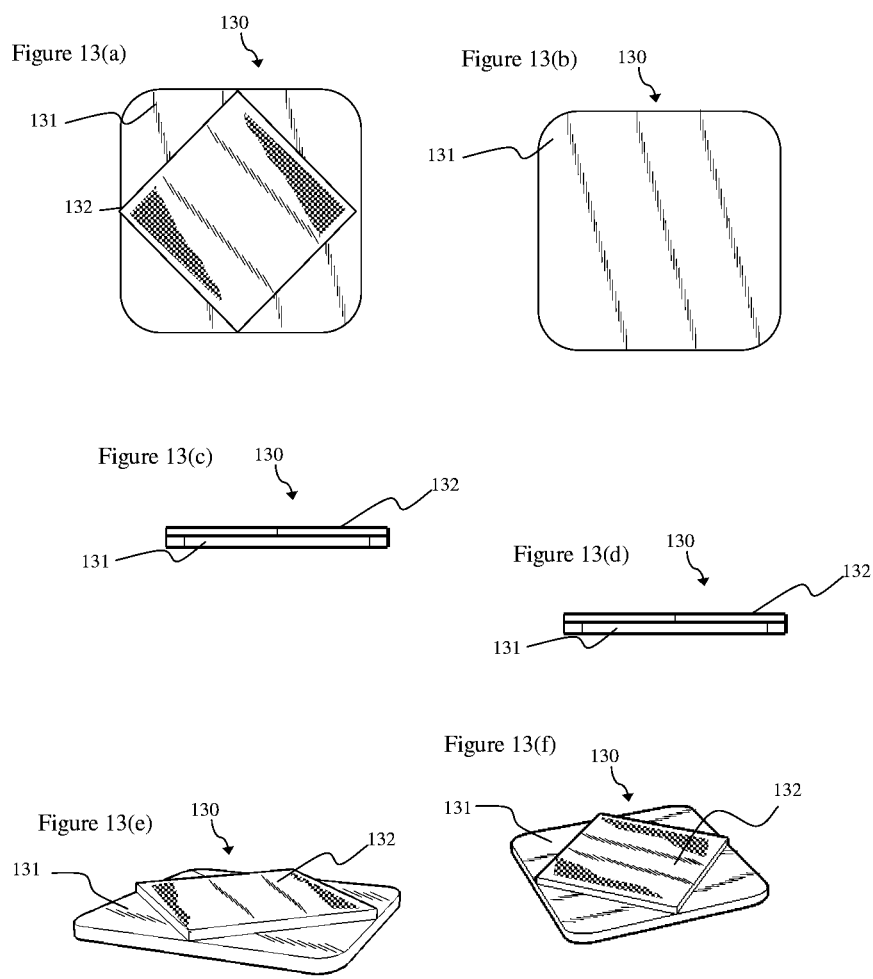

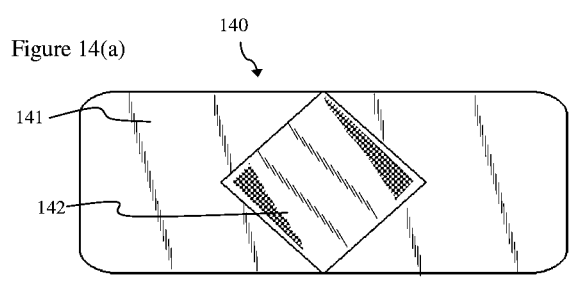
Figure 14(a)
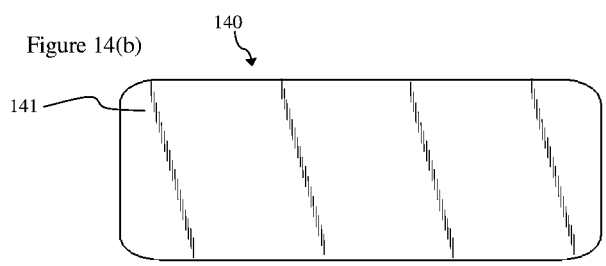
Figure 14(b)
Figure 14(c)
Figure 14(d)
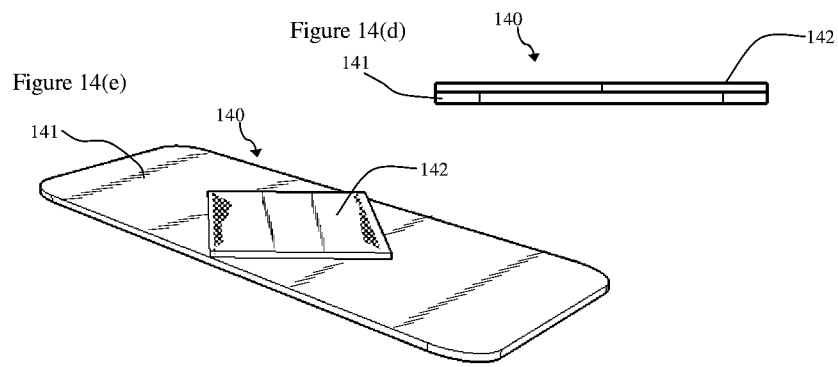
Figure 14(e)

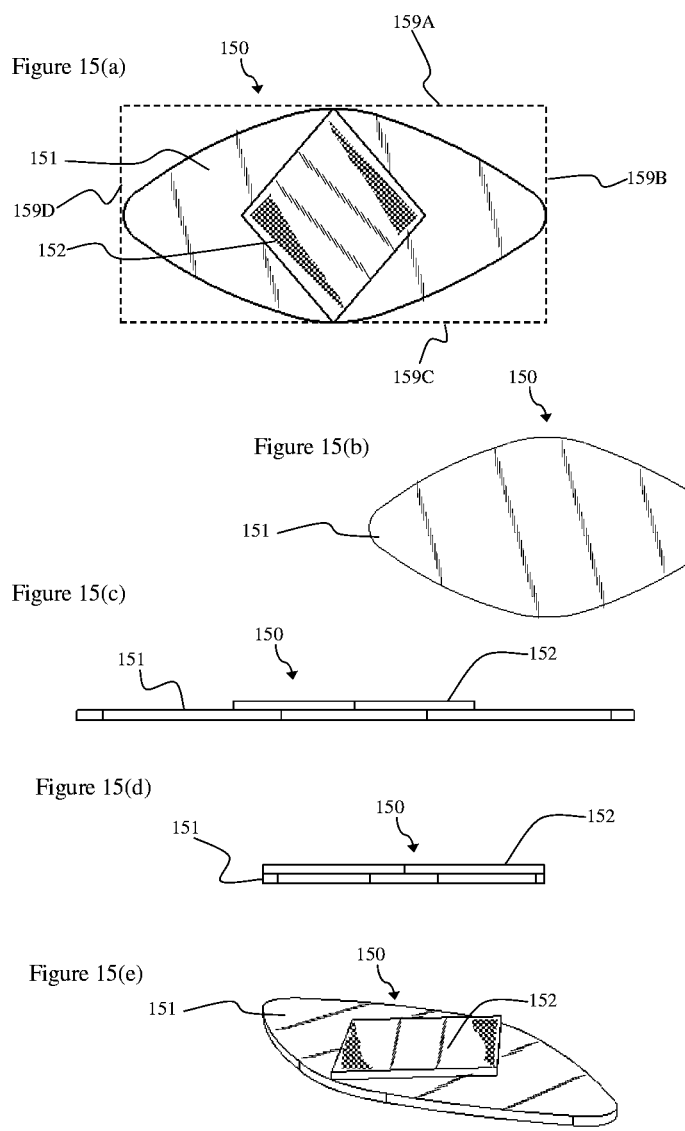

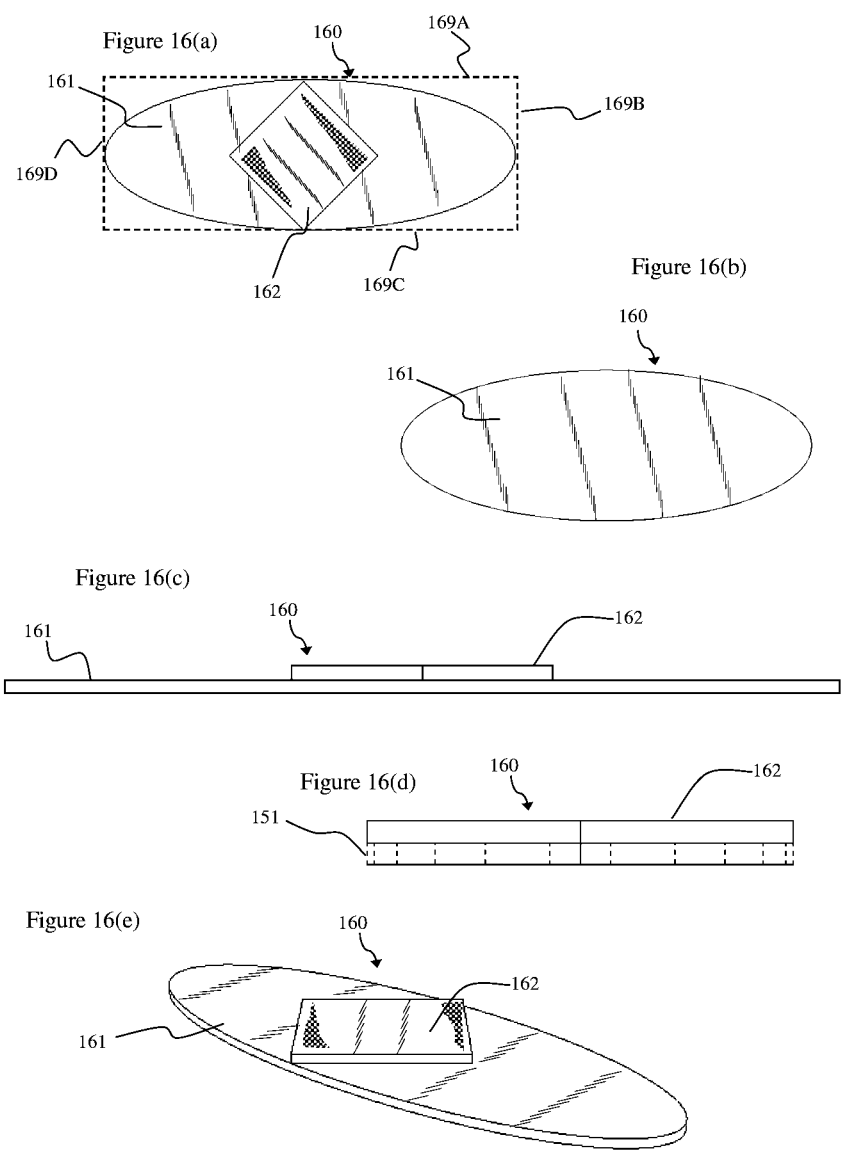

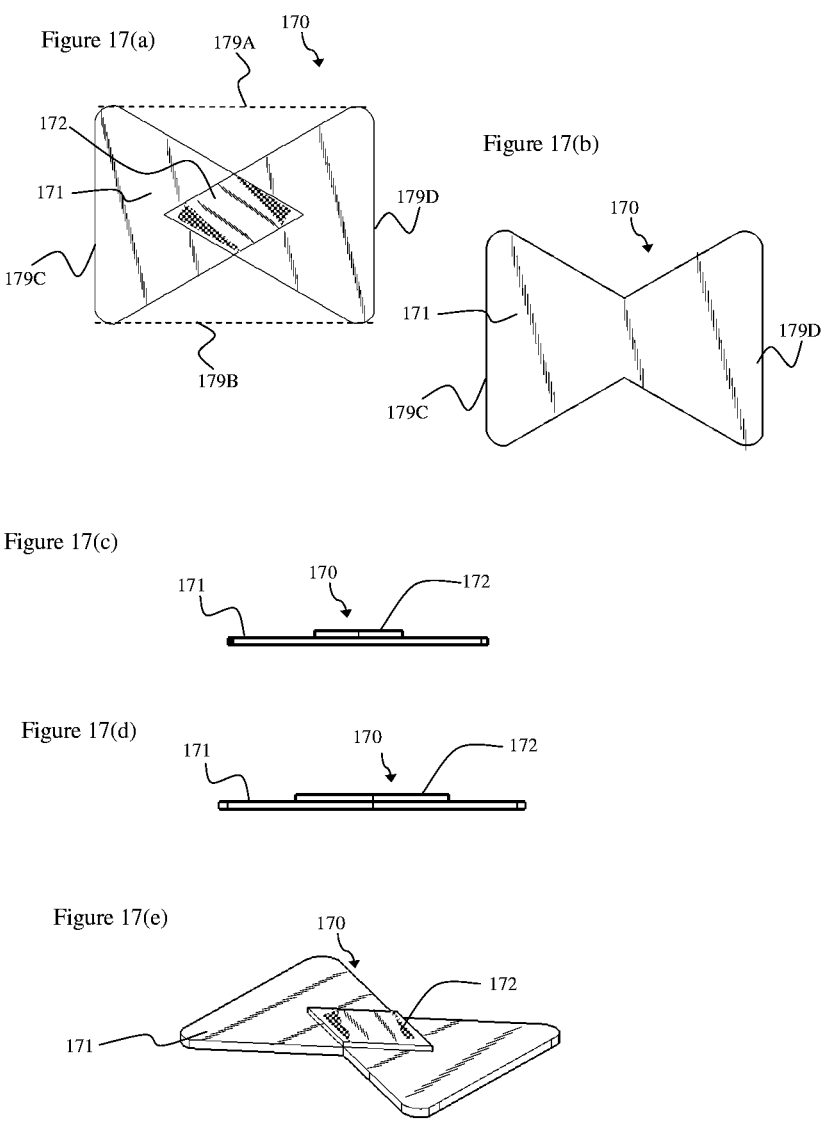

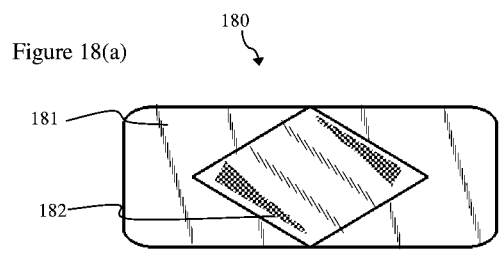
Figure 18(a)
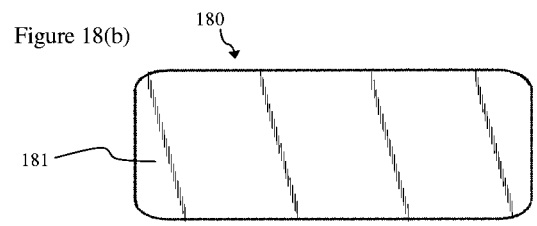
Figure 18(b)
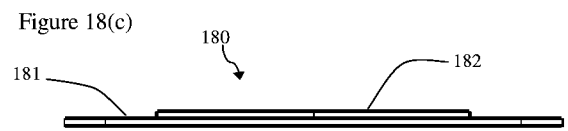
Figure 18(c)
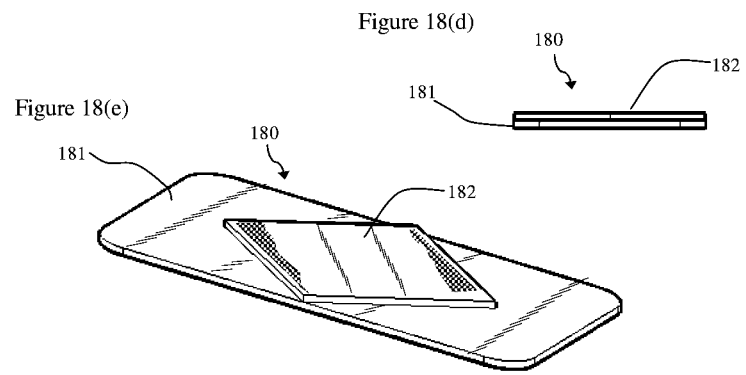
Figure 18(d)
Figure 18(e)

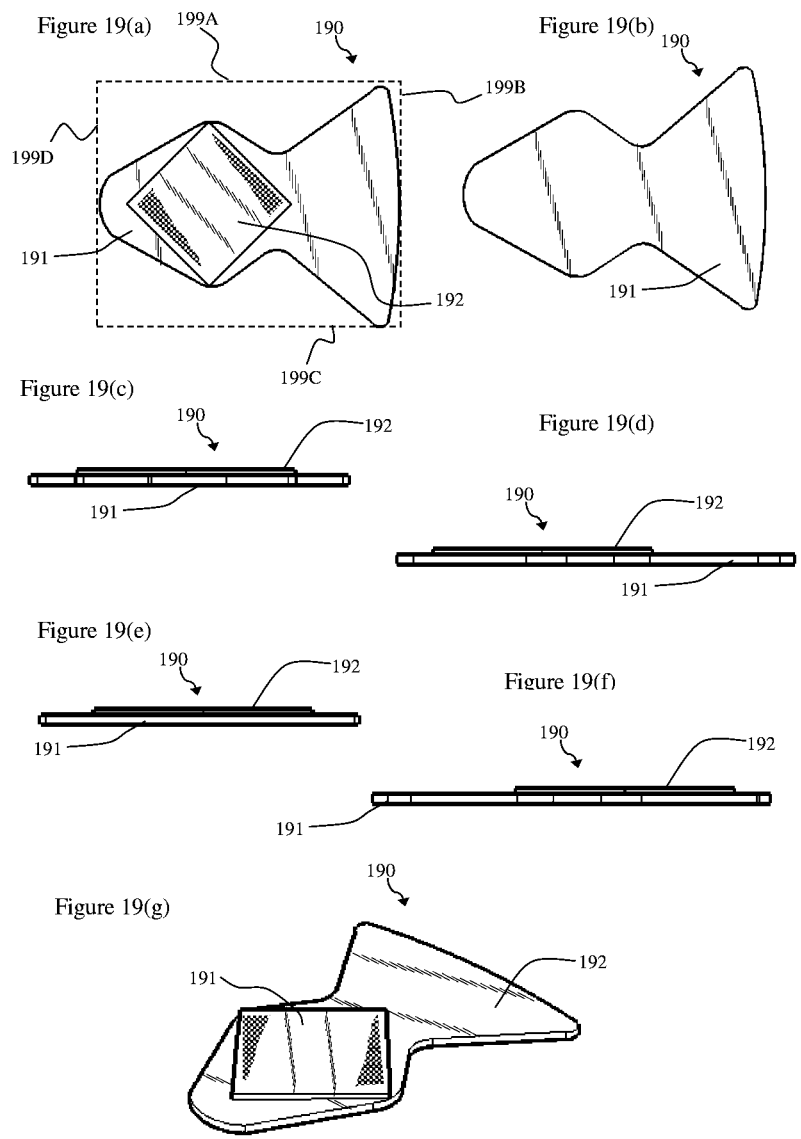

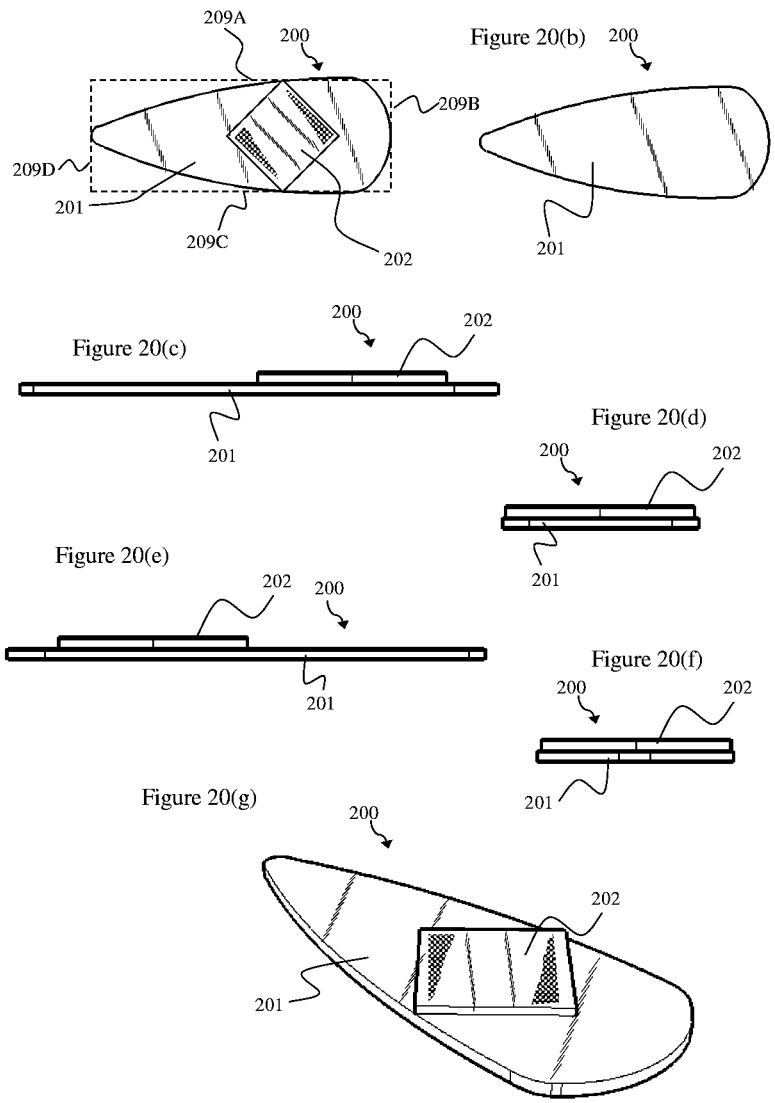

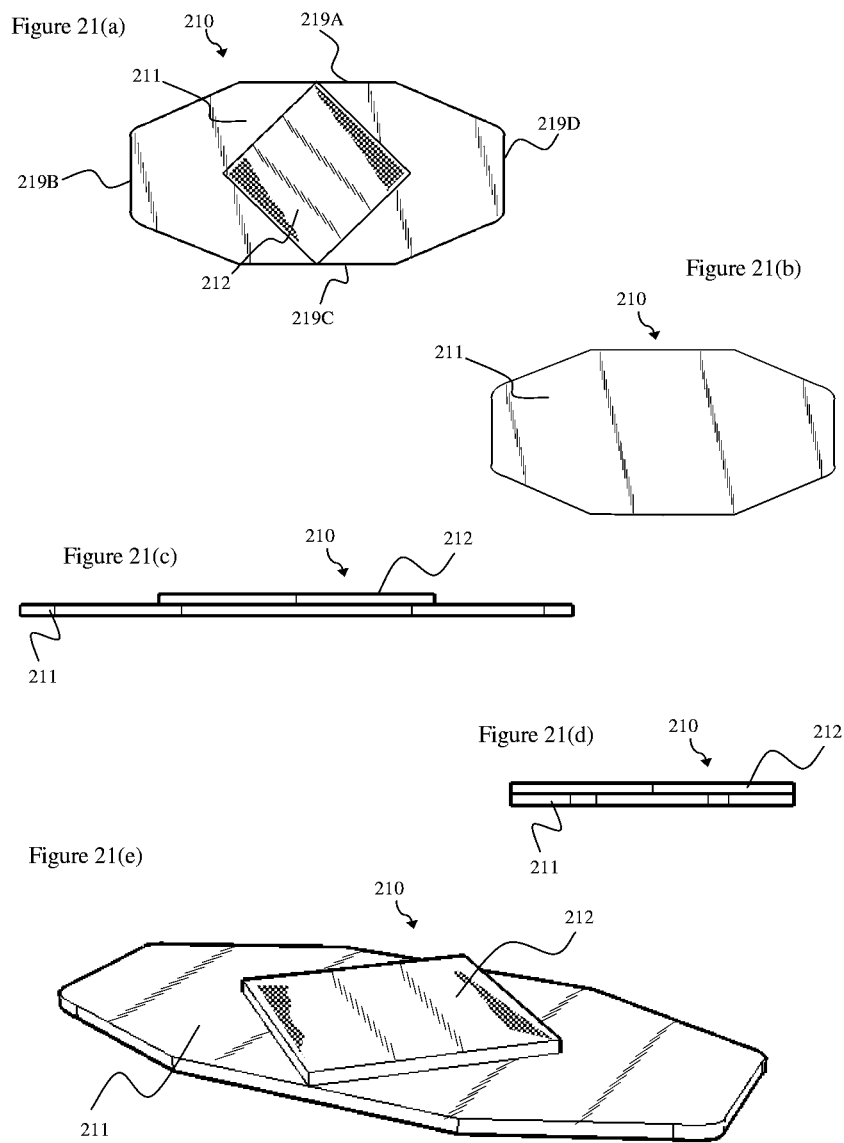

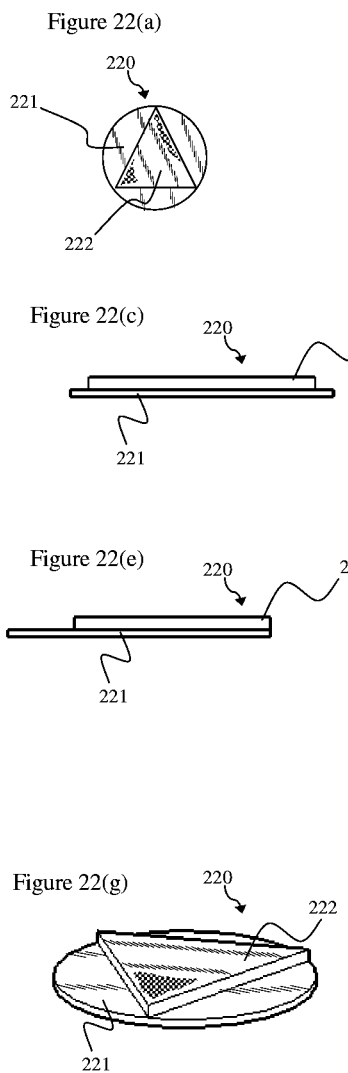

WOUND AND BANDAGE PROTECTION SYSTEM AND METHOD

FIELD OF THE INVENTION

The invention generally relates to a wound and bandage protection system that is designed to resolve many issues of durability, comfort and ease of application that are not adequately resolved by current wound and bandage protection systems. The invention also relates to a method of using the wound and bandage protection system for wound care.

BACKGROUND OF THE INVENTION

Traditional solutions for wound care involve use of gauze and bandages affixed to skin with adhesive, which need to be replaced completely when redressing the wound. This type of wound dressing has numerous shortcomings, in particular for animals with fur. Bandages affixed with adhesive restrict patient movement, and are uncomfortable. Removing the adhesive from skin can be painful, and removing it from fur is not only uncomfortable for an animal, but is also time consuming, and therefore very impractical. However, veterinarians and pet supply stores today almost exclusively sell or use bandages designed for humans for purposes of pet wound care.

One alternative for wound care are self-adhesive wraps that adhere to themselves via a sticky adhesive quality of the wrap material, without sticking to skin or fur. However, a major drawback of these bandages is that they lose the ability to stick when wet or when dirty. The wraps can become undone and unusable in a matter of seconds if licked or tampered with. Therefore, while a good solution for human wound care, these wraps are still impractical for pet wound care.

An additional reason for the need for a comfortable bandage for animals is because they are very prone to infection when healing from a wound, due to the instinct of the animals to lick the location of the wound, leading to the introduction of bacteria and germs to the wound. The animal will also lick and possibly gnaw on bandages as well. Dogs, for example, like the taste of adhesive. The current solution of veterinarians is to place a cone collar around the animal's neck. However, the cone is big, cumbersome and a nuisance for both pet and owner. A dog will swing its head wildly while trying to get the collar off. In the process they can injure themselves; they also find it difficult to navigate when moving about. They also bang into things and knock down everything that is not attached. The cone is a very unpleasant solution.

Therefore, there is a need for a bandaging system that reduces pull on skin and fur, will attach quickly and effortlessly, stay on securely, and be removable and exchangeable without pain.

Furthermore, throughout the history of bandage making, a common problem has plagued the adhesive bandage industry. In order to properly protect a wound, it should be covered and insulated from outside infectants. However, most adhesive bandages do not adequately protect a wound when applied. Makers of older bandages tried to size the gauze pad to allow for a thin strip of adhesive around the gauze pad to adhere to the skin around the wound. However, the strip of adhesive around the gauze pad would often buckle or come loose altogether, and not keep the wound properly sealed, and possibly cause discomfort. Recently companies have tried other solutions. Band-Aid® brand has given up on sealing the wound and has extended the gauze to the edge of the adhesive to maximize the amount of gauze available to cover the wound. Nexcare® has created bandages with extremely small gauze in relation to the bandage, allowing for a better seal, but providing less gauze in the exchange. Furthermore, these bandages tend not to perform well on joints, where the areas of adhesive do not conform to the bending of the limbs without causing a large amount of buckling of the gauze. Therefore, there is a need for a bandaging system to prevent buckling and loosening of the adhesive around the gauze pad of an adhesive bandage, particularly with regard to application of bandages to joints, while at the same time maximizing the amount of gauze available to cover the wound.

SUMMARY OF THE INVENTION

The present invention provides a wound/bandage protection system and a method of use thereof. An exemplary embodiment of a super-stretch tube according to the present invention is disclosed. The super-stretch tube has a strip that extends along a length of the super-stretch tube from a first open end to a second open end of the super-stretch tube at least along an inside surface of the super-stretch tube. The super-stretch tube is preferably made of a super-stretchable elastic non-woven material.

In a first exemplary embodiment of a wound/bandage protector according to the present invention, the wound/bandage protector may be comprised of a body portion, a first-catch fastening surface and a first fastening strap. The body portion is configured as a wrap with a first end, a second end, a wound facing side and a non-wound facing side. The first-catch fastening surface is on an end region, which is proximal to the first end of the body portion, of the non-wound facing side of the body portion. The first-catch fastening surface is configured so as to be capable of fastening with at least a portion of the wound facing side of the body portion. Alternatively, the wound/bandage protector may be configured without the first-catch fastening surface.

The first fastening strap extends from the second end of the body portion and at least a portion of a wound facing side surface of the first fastening strap is configured so as to be capable of fastening with at least a portion of the non-wound facing side of the body portion or a non-wound facing side of the first fastening strap. In one alternative embodiment, the body portion and the first fastening strap may be comprised of the same integral piece of material.

The wound/bandage protector according to the present invention may be configured to be stretchable in a lengthwise direction defined by the first end of the body portion and the second end of the body portion. The first fastening strap of the wound/bandage protector may have a first strap part that is stretchable, and a second strap part. In such an embodiment of the wound/bandage protector according to the present invention, the second strap part may include the portion of the first fastening strap that is capable of fastening with at least a portion of the non-wound facing side of the body portion or the non-wound facing side of the first fastening strap. An elastic modulus of the first strap part may be greater than an elastic modulus of the body portion.

Furthermore, the wound/bandage protector according to the present invention may also have a second fastening strap extending from the second end of the body portion. At least a portion of a wound facing side surface of the second fastening strap is configured so as to be capable of fastening with at least a portion of the non-wound facing side of the body portion and/or a non-wound facing side of the second fastening strap. The second fastening strap may have a first strap part and a second strap part configured in the manner discussed above in reference to the first fastening strap. An elastic modulus of the second fastening strap first strap part may be configured to be greater than an elastic modulus of the body portion.

The wound/bandage protector according to the present invention may also have a strip. The strip may be on the body portion proximal to the first end and extend widthwise. Alternatively, the strip may extend along the length of the body proximal to a top or bottom edge of the body portion. Moreover, multiple strips may be provided, such as strip along both the top and bottom edge of the body portion. The strip may be comprised of a rubberized material exposed on at least the wound facing side of the body portion.

The wound/bandage protector according to the present invention may have a gauze port on the wound facing side of the body portion proximal to the first end of the body portion. The gauze port may be configured to attach to only a small portion of a gauze pad proximal to one side of the gauze pad. The gauze port may be configured so as to allow repeated removable attachment of the gauze pad. The wound/bandage protector may also include a gauze pad. The gauze pad may be configured to attach to the gauze port. Alternatively, the gauze pad may be configured so as to remain adjacent but unattached to the non-wound facing side of the body portion. In such an alternative exemplary embodiment, the gauze pad may have a rubberized or tacky frame on a wound-facing and/or non-wound-facing side of the gauze pad.

The wound/bandage protector according to the present invention may have a strip provided on the body portion preferably between the gauze port and the first end of the body portion. If there is no gauze port, the strip is preferably located proximal to the first end of the body portion. The strip may be comprised of a rubberized material that is exposed at least on the wound facing side of the body portion. Alternatively, all or a portion of the wound-facing side of the body portion may have a tacky surface.

A wound/bandage protector according to the present invention, may have a cover. In such an embodiment of the wound/bandage protector according to the present invention, the body portion has an aperture, and the cover and the aperture are sized so as to allow the cover to completely close the aperture. The body portion may be configured with a shelf surrounding the aperture, and the cover is sized so as to close the aperture by extending at least partially onto the shelf. The wound/bandage protector according to this exemplary embodiment may further comprise a non-stretchable or substantially non-stretchable rim provided on the non-wound-facing side surface of the body portion surrounding the aperture. The surface of the rim is sized and configured so as to allow for removable attachment of the cover.

A wound/bandage protector according to the present invention, may have dead-zones periodically provided along the length of the body portion. The dead zones may be configured to extend widthwise with respect to the length of the bandage and provided, preferably, at least every 3 inches along the length of the body portion.

A wound/bandage protector according to the present invention, may have a gauze panel positioned on or integrated into the body portion proximal to the first end of the body portion. The gauze panel may be configured so as to allow for attachment and/or repeated attachment of a gauze pad on the wound-facing side of the body portion. The gauze panel may be sized so as to allow all or substantially all of the gauze pad to be attached or removably attached to the gauze panel. The gauze panel and the part of the body portion on which the gauze panel is positioned or integrated may be configured as a dead zone. Alternatively, the gauze pad and the gauze panel may be comprised of stretchable material.

In one exemplary embodiment of a bandage according to the present invention, the bandage is comprised of a stretchable body portion with a stretchable gauze pad affixed to the wound-facing side of the body portion. The body portion has adhesive on at least a portion of a wound facing side or, alternatively, the body portion is comprised of self adherent material.

In another exemplary embodiment of a bandage according to the present invention, the bandage has a body portion and a gauze pad on a wound-facing side of the body portion. The gauze pad is shaped and positioned on the body portion in such manner that the bandage is configured as a "diamond gauze" adhesive bandage. The body portion has adhesive on at least a portion of a wound facing side or, alternatively, the body portion is comprised of self adherent material.

In another exemplary embodiment of a bandage according to the present invention, the bandage is a "diamond gauze" bandage that has a body portion and a gauze pad. The body portion has adhesive on at least a portion of a wound facing side or, alternatively, the body portion is comprised of self adherent material. The gauze pad is shaped as a square, rhombus or parallelogram and oriented on the wound-facing side of the body portion in such manner that each of the corners of the gauze pad are oriented towards a different length tangent or width tangent of the adhesive bandage.

In another exemplary embodiment of a bandage according to the present invention the bandage further includes a cover. The body portion has an aperture, and the cover and the aperture are sized so as to allow the cover to completely close the aperture. The body portion may also be configured with a shelf surrounding the aperture. In such an embodiment, the cover is sized so as to close the aperture by extending at least partially onto the shelf.

In another exemplary embodiment of a wound/bandage protector according to the present invention, the wound/bandage protector may be comprised of a body, a fastening strap and a cover. The body is comprised of stretchable material and configured as a sock/mitten with a first end that is open, a second end that is closed, an internal wound facing side and an external non-wound facing side. The body may also have a panel with little or no stretch. The fastening strap is comprised of a first strap part and a second strap part. The first strap part is connected to the body and comprised of stretchable material. The second strap part is connected to the first strap part. At least a portion of a wound-facing side of the second strap part is configured so as to be capable of fastening with at least a portion of the external non-wound facing side of the body, at least a portion of a non-wound facing side of the first strap part, and at least a portion of a non-wound facing side of the second strap part. The fastening strap may also have a third strap part that is configured as a dead zone connecting the first strap part to the external non-wound facing side of the body. The fastening strap may also have a fourth strap part that is configured as a dead zone connecting the first strap part and the second strap part. Both the third strap part and the fourth strap part have a rubberized or tacky surface exposed on at least the wound facing side of the fastening strap.

The wound/bandage protector, according to this exemplary embodiment, may also include a sheath with a first open end, and a second closed end, the sheath sized and configured to fit over an entirety of the body of the wound/bandage protector. A slot or slit in the sheath is sized and positioned so as to allow the fastening strap to fit therethrough. The fastening strap is sized so as to be capable of extending around an outside of the sheath to secure both the body and the sheath to an appendage being bandaged by fastening the wound facing side of the second strap part to a non-wound facing side of the fastening strap.

In another exemplary embodiment of a bandage according to the present invention the bandage further includes a cover. The body portion has an aperture, and the cover and the aperture are sized so as to allow the cover to completely close the aperture. The body portion may also be configured with a shelf surrounding the aperture. In such an embodiment, the cover is sized so as to close the aperture by extending at least partially onto the shelf.

In another exemplary embodiment of a bandage according to the present invention, the bandage has a body portion a cover and a rim. The body portion has an aperture, and the cover and the aperture are sized so as to allow the cover to completely close the aperture. The rim, which is on a non-wound-facing side surface of the body portion surrounding the aperture, is preferably non-stretchable or substantially non-stretchable. The surface of the rim is sized and configured so as to allow for removable attachment of the cover.

In another exemplary embodiment of a bandage according to the present invention, the bandage has a body portion and a cover. The body portion has an aperture shaped as a square, rhombus or parallelogram that is oriented in such manner that each of the corners of the aperture are oriented towards a different length tangent or width tangent of the adhesive bandage. The cover is sized to completely close the aperture.

In another exemplary embodiment of a bandage according to the present invention, the bandage is a "triangular gauze" bandage that has a triangular shaped body portion and a triangular shaped gauze pad. The triangular shaped body portion has adhesive on at least a portion of a wound facing side. The triangular shaped gauze pad is oriented on the wound-facing side of the body portion in such manner that each of the corners of the gauze pad is oriented toward a different side of the adhesive bandage. The triangular shaped gauze pad may be oriented on the wound-facing side of the body portion in such manner that each of the corners of the gauze pad is oriented toward a mid-point or a mid-section of a different side of the adhesive bandage.

In another exemplary embodiment of a bandage according to the present invention, the bandage is a "triangular gauze" bandage that has a circular shaped body portion and a triangular shaped gauze pad. The circular shaped body portion has adhesive on at least a portion of a wound facing side. The triangular shaped gauze pad is provided on the wound-facing side of the body portion.

The present invention also discloses methods of protecting wounds using the bandage/wound protectors, bandages and super-stretch tubes, such as the exemplary embodiments of those disclosed herein. Thus, for example, a bandage with an aperture may be used to protect a wound by applying the bandage with the aperture opened, placing gauze and medicine on the wound; and closing the aperture of the bandage. The method may also be applied with wound/bandage protector with an aperture. In addition, a wound/bandage protector or super stretch tube may be positioned over the bandage or wound/bandage protector with the aperture. Similarly with all the bandages and wound/bandage protectors disclosed herein, the bandage or wound/bandage protector may first be placed over the wound and then a wound/bandage protector or super stretch tube may be positioned over the bandage or wound/bandage protector. In addition, the invention also relates to a kit that includes all or a set of the wound/bandage protectors, bandages, and/or super-stretch tubes, as disclosed herein.

BRIEF DESCRIPTION OF THE DRAWINGS

FIG. 1(*b*) illustrates an exemplary embodiment of a cross-sectional view of the super-stretch tube taken along the line I-I' in FIG. 1(*a*);

FIG. 2(*a*) is a side view of an exemplary embodiment of a bandage/wound protector according to the present invention;

FIG. 2(*b*) is a side view of an exemplary embodiment of a protective sheath for the bandage/wound protector illustrated in FIG. 2(*a*);

FIG. 2(*c*) is a side view of the exemplary embodiment of the bandage/wound protector illustrated in FIG. 2(*a*) illustrating the process of securing the bandage/wound protector;

FIG. 3(*b*) is a side view of an exemplary embodiment of a protective sheath for the bandage/wound protector illustrated in FIG. 3(*a*);

FIG. 6(*a*) is a top non-wound facing side view of an exemplary embodiment of a bandage/wound protector according to the present invention;

FIG. 6(*b*) is a bottom wound facing side view of the exemplary embodiment of the bandage/wound protector illustrated in FIG. 6(*a*);

FIG. 6(*c*) is a side cross-sectional view of the exemplary embodiment of the bandage/wound protector illustrated in FIGS. 6(*a*) and (*b*) taken along the line II-II' in FIG. 6(*b*);

FIG. 7(*a*) is a top non-wound facing side view of an exemplary embodiment of a bandage/wound protector according to the present invention;

FIG. 7(*b*) is a bottom wound facing side view of the exemplary embodiment of the bandage/wound protector illustrated in FIG. 7(*a*);

FIG. 7(*c*) is a side cross-sectional view of the exemplary embodiment of the bandage/wound protector illustrated in FIGS. 7(*a*) and (*b*) taken along the line III-III' in FIG. 7(*b*);

FIG. 8(*a*) is a top non-wound facing side view of an exemplary embodiment of a bandage/wound protector according to the present invention;

FIG. 8(*b*) is a bottom wound facing side view of the exemplary embodiment of the bandage/wound protector illustrated in FIG. 8(*a*);

FIG. 8(*c*) is a side cross-sectional view of the exemplary embodiment of the bandage/wound protector illustrated in FIGS. 8(*a*) and (*b*) taken along the line IV-IV' in FIG. 8(*b*);

FIG. 9(*a*) is a top non-wound facing side view of an exemplary embodiment of a bandage/wound protector according to the present invention;

FIG. 9(*b*) is a bottom wound facing side view of the exemplary embodiment of the bandage/wound protector illustrated in FIG. 9(*a*);

FIG. 9(*c*) is a side cross-sectional view of the exemplary embodiment of the bandage/wound protector illustrated in FIGS. 9(*a*) and (*b*) taken along the line V-V' in FIG. 9(*b*);

FIG. 10(*b*) is a bottom wound facing side view of the exemplary embodiment of the bandage/wound protector illustrated in FIG. 10(*a*);

FIG. 12(a) shows a bottom wound-facing side of an exemplary embodiment of a "diamond gauze" adhesive bandage according to the present invention;

FIG. 12(b) shows a top non-wound-facing side of the exemplary embodiment of the "diamond gauze" adhesive bandage illustrated in FIG. 12(a);

FIG. 12(c) shows a side view of the exemplary embodiment of the "diamond gauze" adhesive bandage illustrated in FIGS. 12(a) and (b) (the view from the other side is a minor image);

FIG. 12(d) shows an end view of the exemplary embodiment of the "diamond gauze" adhesive bandage illustrated in FIGS. 12(a) and (b) (the view from the other side is a minor image);

FIG. 12(e) shows a perspective view of the exemplary embodiment of the "diamond gauze" adhesive bandage illustrated in FIGS. 12(a) and (b);

FIG. 12(f) shows a second perspective view of the exemplary embodiment of the "diamond gauze" adhesive bandage illustrated in FIGS. 12(a) and (b);

FIG. 13(a) shows a bottom wound-facing side of an exemplary embodiment of a "diamond gauze" adhesive bandage according to the present invention;

FIG. 13(b) shows a top non-wound-facing side of the exemplary embodiment of the "diamond gauze" adhesive bandage illustrated in FIG. 13(a);

FIG. 13(c) shows a side view of the exemplary embodiment of the "diamond gauze" adhesive bandage illustrated in FIGS. 13(a) and (b) (the view from the other side is a minor image);

FIG. 13(d) shows an end view of the exemplary embodiment of the "diamond gauze" adhesive bandage illustrated in FIGS. 13(a) and (b) (the view from the other side is a minor image);

FIG. 13(e) shows a perspective view of the exemplary embodiment of the "diamond gauze" adhesive bandage illustrated in FIGS. 13(a) and (b);

FIG. 13(f) shows a second perspective view of the exemplary embodiment of the "diamond gauze" adhesive bandage illustrated in FIGS. 13(a) and (b);

FIG. 14(a) shows a bottom wound-facing side of an exemplary embodiment of a "diamond gauze" adhesive bandage according to the present invention;

FIG. 14(b) shows a top non-wound-facing side of the exemplary embodiment of the "diamond gauze" adhesive bandage illustrated in FIG. 14(a);

FIG. 14(c) shows a side view of the exemplary embodiment of the "diamond gauze" adhesive bandage illustrated in FIGS. 14(a) and (b) (the view from the other side is a mirror image);

FIG. 14(d) shows an end view of the exemplary embodiment of the "diamond gauze" adhesive bandage illustrated in FIGS. 14(a) and (b) (the view from the other side is a mirror image);

FIG. 14(e) shows a perspective view of the exemplary embodiment of the "diamond gauze" adhesive bandage illustrated in FIGS. 14(a) and (b);

FIG. 15(a) shows a bottom wound-facing side of an exemplary embodiment of a "diamond gauze" adhesive bandage according to the present invention;

FIG. 15(b) shows a top non-wound-facing side of the exemplary embodiment of the "diamond gauze" adhesive bandage illustrated in FIG. 15(a);

FIG. 15(c) shows a side view of the exemplary embodiment of the "diamond gauze" adhesive bandage illustrated in FIGS. 15(a) and (b) (the view from the other side is a mirror image);

FIG. 15(d) shows an end view of the exemplary embodiment of the "diamond gauze" adhesive bandage illustrated in FIGS. 15(a) and (b) (the view from the other side is a mirror image);

FIG. 15(e) shows a perspective view of the exemplary embodiment of the "diamond gauze" adhesive bandage illustrated in FIGS. 15(a) and (b);

FIG. 16(a) shows a bottom wound-facing side of an exemplary embodiment of a "diamond gauze" adhesive bandage according to the present invention;

FIG. 16(b) shows a top non-wound-facing side of the exemplary embodiment of the "diamond gauze" adhesive bandage illustrated in FIG. 16(a);

FIG. 16(c) shows a side view of the exemplary embodiment of the "diamond gauze" adhesive bandage illustrated in FIGS. 16(a) and (b) (the view from the other side is a mirror image);

FIG. 16(d) shows an end view of the exemplary embodiment of the "diamond gauze" adhesive bandage illustrated in FIGS. 16(a) and (b) (the view from the other side is a mirror image);

FIG. 16(e) shows a perspective view of the exemplary embodiment of the "diamond gauze" adhesive bandage illustrated in FIGS. 16(a) and (b);

FIG. 17(a) shows a bottom wound-facing side of an exemplary embodiment of a "diamond gauze" adhesive bandage according to the present invention;

FIG. 17(b) shows a top non-wound-facing side of the exemplary embodiment of the "diamond gauze" adhesive bandage illustrated in FIG. 17(a);

FIG. 17(c) shows a side view of the exemplary embodiment of the "diamond gauze" adhesive bandage illustrated in FIGS. 17(a) and (b) (the view from the other side is a minor image);

FIG. 17(d) shows an end view of the exemplary embodiment of the "diamond gauze" adhesive bandage illustrated in FIGS. 17(a) and (b) (the view from the other side is a minor image);

FIG. 17(e) shows a perspective view of the exemplary embodiment of the "diamond gauze" adhesive bandage illustrated in FIGS. 17(a) and (b);

FIG. 18(a) shows a bottom wound-facing side of an exemplary embodiment of a "diamond gauze" adhesive bandage according to the present invention;

FIG. 18(b) shows a top non-wound-facing side of the exemplary embodiment of the "diamond gauze" adhesive bandage illustrated in FIG. 18(a);

FIG. 18(c) shows a side view of the exemplary embodiment of the "diamond gauze" adhesive bandage illustrated in FIGS. 18(a) and (b) (the view from the other side is a minor image);

FIG. 18(d) shows an end view of the exemplary embodiment of the "diamond gauze" adhesive bandage illustrated in FIGS. 18(a) and (b) (the view from the other side is a minor image);

FIG. 18(e) shows a perspective view of the exemplary embodiment of the "diamond gauze" adhesive bandage illustrated in FIGS. 18(a) and (b);

FIG. 19(a) shows a bottom wound-facing side of an exemplary embodiment of a "diamond gauze" adhesive bandage according to the present invention;

FIG. 19(b) shows a top non-wound-facing side of the exemplary embodiment of the "diamond gauze" adhesive bandage illustrated in FIG. 19(a);

FIG. 19(c) shows a first side view of the exemplary embodiment of the "diamond gauze" adhesive bandage illustrated in FIGS. 19(a) and (b);

FIG. 19(d) shows a second side view of the exemplary embodiment of the "diamond gauze" adhesive bandage illustrated in FIGS. 19(a) and (b);

FIG. 19(e) shows a first end view of the exemplary embodiment of the "diamond gauze" adhesive bandage illustrated in FIGS. 19(a) and (b);

FIG. 19(f) shows a second end view of the exemplary embodiment of the "diamond gauze" adhesive bandage illustrated in FIGS. 19(a) and (b);

FIG. 19(g) shows a perspective view of the exemplary embodiment of the "diamond gauze" adhesive bandage illustrated in FIGS. 19(a) and (b);

FIG. 20(a) shows a bottom wound-facing side of an exemplary embodiment of a "diamond gauze" adhesive bandage according to the present invention;

FIG. 20(b) shows a top non-wound-facing side of the exemplary embodiment of the "diamond gauze" adhesive bandage illustrated in FIG. 20(a);

FIG. 20(c) shows a first side view of the exemplary embodiment of the "diamond gauze" adhesive bandage illustrated in FIGS. 20(a) and (b);

FIG. 20(d) shows a second side view of the exemplary embodiment of the "diamond gauze" adhesive bandage illustrated in FIGS. 20(a) and (b);

FIG. 20(e) shows a first end view of the exemplary embodiment of the "diamond gauze" adhesive bandage illustrated in FIGS. 20(a) and (b);

FIG. 20(f) shows a second end view of the exemplary embodiment of the "diamond gauze" adhesive bandage illustrated in FIGS. 20(a) and (b);

FIG. 20(g) shows a perspective view of the exemplary embodiment of the "diamond gauze" adhesive bandage illustrated in FIGS. 20(a) and (b);

FIG. 21(a) shows a bottom wound-facing side of an exemplary embodiment of a "diamond gauze" adhesive bandage according to the present invention;

FIG. 21(b) shows a top non-wound-facing side of the exemplary embodiment of the "diamond gauze" adhesive bandage illustrated in FIG. 21(a);

FIG. 21(c) shows a side view of the exemplary embodiment of the "diamond gauze" adhesive bandage illustrated in FIGS. 21(a) and (b) (the view from the other side is a mirror image);

FIG. 21(d) shows an end view of the exemplary embodiment of the "diamond gauze" adhesive bandage illustrated in FIGS. 21(a) and (b) (the view from the other side is a mirror image);

FIG. 21(e) shows a perspective view of the exemplary embodiment of the "diamond gauze" adhesive bandage illustrated in FIGS. 21(a) and (b);

FIG. 22(a) shows a bottom wound-facing side of an exemplary embodiment of a "triangular gauze" adhesive bandage according to the present invention;

FIG. 22(b) shows a top non-wound-facing side of the exemplary embodiment of the "triangular gauze" adhesive bandage illustrated in FIG. 22(a);

FIG. 22(c) shows a first side view of the exemplary embodiment of the "triangular gauze" adhesive bandage illustrated in FIGS. 22(a) and (b);

FIG. 22(d) shows a second side view of the exemplary embodiment of the "triangular gauze" adhesive bandage illustrated in FIGS. 22(a) and (b);

FIG. 22(e) shows a first end view of the exemplary embodiment of the "triangular gauze" adhesive bandage illustrated in FIGS. 22(a) and (b);

FIG. 22(f) shows a second end view of the exemplary embodiment of the "triangular gauze" adhesive bandage illustrated in FIGS. 22(a) and (b);

FIG. 22(g) shows a perspective view of the exemplary embodiment of the "triangular gauze" adhesive bandage illustrated in FIGS. 22(a) and (b);

DETAILED DESCRIPTION OF THE INVENTION

Figure 1A:
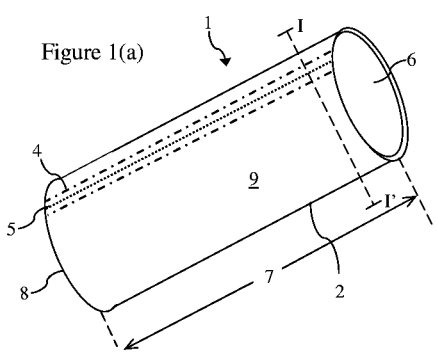
FIG. 1(*a*) is a perspective side view of an exemplary embodiment of a super-stretch tube according to the present invention.

FIG. 1 shows a super-stretch tube 1 that is part of the bandaging system according to the present invention. The super-stretch tube 1 may be used for protecting a wound or for covering one of the bandages disclosed below. The super-stretch tube 1 has a tube body portion 2 which may be made of a stretchable material such as an elastic non-woven that is found in the side portions of Huggies® brand Little Swimmers® and Pull-Ups® or Pampers® Easy Ups® Cruisers®. Alternatively, the tube body portion 2 may be made of other materials with similar elasticity properties that provide a comparable amount of stretchability and tension.

According to one exemplary embodiment of the invention, the stretchable material of the tube body portion 2, when extended to its full capacity, can stretch to more than double the tube body portion's 2 un-extended size. In the context of this application, "super stretchable" material refers to material that can resiliently stretch to a length that is equal to or greater than one and a half times the length of the material when not under tension. In the context of this application, "stretchable" material refers to material that can resiliently stretch to a length that is at least ten percent greater than the length of the material when not under tension. A material that has "little or no stretch" is one that is not super stretchable. A material that has "no stretch" is one that is not stretchable. A "dead zone" is an area of material that has little or no stretch which may, but not necessarily, be an integral part of an otherwise stretchable material. A dead zone area may be formed in an elastic nonwoven material with an ultrasonic seal, which is generally used when attaching two nonwovens together, by punching, applying pressure and then high frequency vibration, which causes nonwoven materials to melt, to an overlapping connecting portion of the two nonwovens. Alternatively, particularly when forming a dead zone in a single piece of nonwoven fabric, the dead zone may be formed by simply applying the pressure and high frequency vibration without punching. The "stretching resistance", "elastic modulus" or Young's modulus, refers to a ratio of stretching force on a particular area along a particular axis over a ratio of change in the length of the material along the particular axis due to the applied stretching force. Thus, a material that can be "easily" stretched has a lower elastic modulus than a material that is "hard" to stretch. The stretchable material of the tube body portion 2 at least provides stretching capacity in a manner that allows a circumference of the super-stretch tube 1 to vary. The stretchable material of the tube body portion 2 may, alternatively, provide stretching capacity that allows both the circumference and a length of the tube body portion 2 to vary. Preferably, the super-stretch material of the tube body portion 2 is very thin, being less than $1/16^{th}$ of an inch thick when in the un-extended position and provides some breathability as well as good water resistance.

The super-stretch tube 1 has a strip 4 that extends along a length 7 of the super-stretch tube 1 from a first open end 6 of the super-stretch tube 1 to a second open end 8 of the super-stretch tube 1 at least along an inside surface 3 of the super-stretch tube 1. The strip 4 may be positioned along or over a seam 5 that may extend the length of the super-stretch tube 1. The strip 4 has one or more threads made of a rubberized material provided in such a manner that the rubberized material threads are exposed at least on an inner side of the super-stretch tube 1. The strip 4 may be made from an elastic material used in some larger hair bands that includes rubberized material threads. The rubberized material is not necessarily exposed on the exterior side 9 of the stretch tube 1. Alternatively, the strip 4 may be comprised of stretch non-slip medical grade silicone or similar, preferably latex free, material. The non-slip silicone may be applied in a continuous or discontinuous manner to form the strip 4. Alternatively, the entire inside of the tube may be coated with low tack non-slip silicone or similar, preferably latex free, material.

Figure 1B:
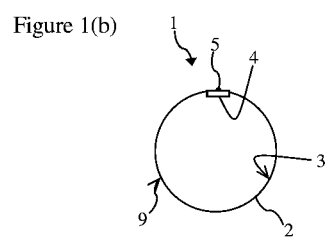

Although not depicted in FIGS. 1(a) and 1(b) of the super-stretch tube 1, in an alternative exemplary embodiment of the super-stretch tube 1 according to the present invention, there may also be one or more super-stretch tube fastening straps attached to an exterior surface 9 of the super-stretch tube 1. The one or more super-stretch tube fastening straps may be configured in a similar fashion as fastening strap 23A shown in FIGS. 2(a) and 2(c) and discussed below. Preferably, a first fastening strap of the one or more super-stretch tube fastening straps may be provided in close proximity to the first open end 6 of the super-stretch tube 1 and a second fastening strap of the one or more of the super-stretch tube fastening straps may be provided in close proximity to the to the second open end 8 of the super-stretch tube 1.

FIG. 2(a) shows an exemplary embodiment of a wound/bandage protector 20, according to the present invention. The wound/bandage protector 20 is configured as a "sock/mitten", with a body 21 that has a first end 21A that is open and a second end 21B that is closed. The body 21 may be made of super-stretchable or stretchable material similar to the material of the super-stretch tube 1, discussed above and shown in FIG. 1 and at least a portion of the non-wound facing side of the body 21 may be configured as a loop portion of a hook and loop type fastener. The stretchable material of the body 21 of the wound/bandage protector 20 at least provides such stretching capacity in a manner that allows a circumference of the body 21 to vary. The stretchable material of the body 21 may, alternatively, provide such stretching capacity that allows both the circumference and a length of the body 21 to vary.

The body 21 has a panel 22 which may be made of material that has little or no stretch. The panel 22 is shown in FIG. 2(*a*), which illustrates an outside side view showing a portion of an external non-wound facing surface of the wound/bandage protector 20. However, the panel 22 may not be visibly distinguishable from the rest of the body 21, particularly on the external non-wound facing surface of the wound/bandage protector 20. A gauze pad (not specifically illustrated in FIG. 2(*a*) may be affixed to the panel 22 on an internal wound-facing side. Alternatively, the gauze pad may be attached to the panel 22 in a temporary fashion such as via use of a hook and loop type fastening system or a reusable pressure sensitive adhesive such as that used in Post-it® notes. In another alternative embodiment, the panel 22 and the gauze pad is made of stretchable or super-stretchable material. In this embodiment, the entire body 21 may be configured to function as the panel 22.

In the context of this specification, gauze, or gauze pad, refers to any material or composite of material that may be therapeutically used as a pad over a wound. For example, the gauze pad may be made of cotton or a polyester blend fabric. The fabric may be covered with a plastic porous film such as Telfa® which prevents or minimizes wound adhesion. Furthermore, the gauze pad may be backed with a film that prevents body fluids from penetrating through the gauze pad to the bandage.

The body 21 has an external non-wound facing surface and an internal wound-facing surface. Attached to the external non-wound facing surface of the body 21 proximate to the first end 21A is a fastening strap 23A. The fastening strap 23A, as illustrated in FIG. 2(*a*) has a first strap part 23 that may be attached to the body 21 via a first attachment region 24. The first strap part 23 may be comprised of a stretchable or super stretchable material similar to the material used in the super-stretch tube 1. The material of the first strap part 23 preferably provides a stretching resistance that is greater than the stretching resistance of the body 21. The material of the first strap part 23 at least provides such stretching capacity in a manner that allows the length of the fastening strap 23A to vary. The first attachment region 24 is preferably configured as a dead zone to provide no stretch and may be comprised of a composite of the material of the first strap part 23 and the body 21 of the wound/bandage protector 20 and may be attached by a punch and melt heat seal. Alternatively, the first strap part 23 is directly attached to the body 21 without the first attachment region 24 intervening therebetween.

A second strap part 27 is attached to the first strap part 23 via a second attachment region 25. The second attachment region 25 is preferably configured as a dead zone to provide no stretch and may be comprised of a composite of the material of the first strap part 23 and the second strap part 27 and may be attached by a punch and melt heat seal. Alternatively, the second strap part 27 is directly attached to the first strap part 23 without the second attachment region 25 intervening therebetween. The fastening strap 23A has a wound facing side, which may be seen in FIG. 2(*a*). The second strap part 27 has a portion 26 that has a hook portion of a hook and loop type fastener on a wound-facing side of the fastening strap 23A.

FIG. 2(*c*) illustrates the process of securing the bandage/wound protector 20 of FIG. 2(*a*) by showing the fastening strap 23A in an intermediate position, as the fastening strap 23A is being extended around the external non-wound facing surface of the bandage/wound protector 20 in the direction indicated by arrow 27A. The fastening strap 23A has a non-wound facing side, which may be seen in FIG. 2(*c*). The first strap part 23 may be configured to act as a loop portion of a hook and loop type fastener on the non-wound facing side of the first strap part 23. The second strap part 27 may be configured as a loop portion of a hook and loop type fastener on the non-wound facing side of the fastening strap 23A.

The wound/bandage protector 20 may be slipped onto an appendage through the opening on the first end 21A of the body 21 so that the gauze pad that is affixed to the panel 22 of the wound/bandage protector 20 covers a wound on the appendage, and the wound/bandage protector 20 is then secured in place by wrapping the fastening strap 23A around the outside of the wound/bandage protector 20 and affixing the portion 26 of the second strap part 27 to the loop portion of the first strap part 23, the body 21, or the loop portion of the second strap part 27.

Figure 3A:
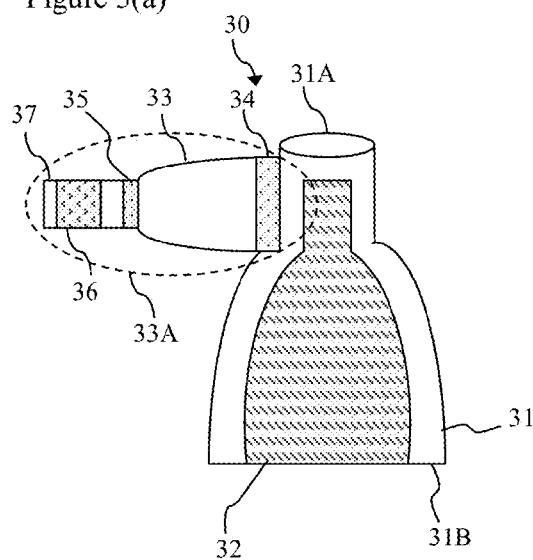
FIG. 3(*a*) is a side view of an exemplary embodiment of a bandage/wound protector according to the present invention.
Figure 3B:
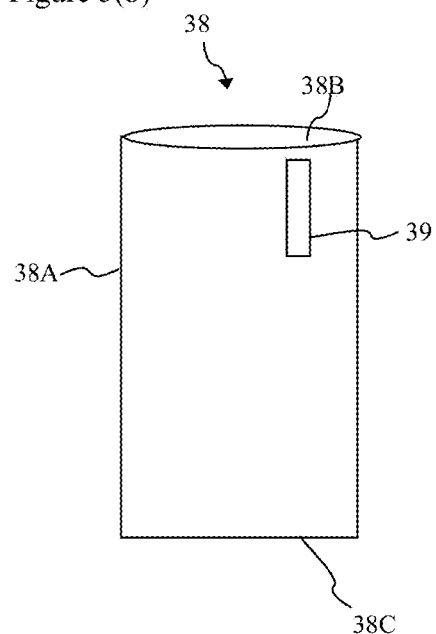

FIG. 3(*a*) shows an exemplary embodiment of a wound/bandage protector 30, according to the present invention. The wound/bandage protector 30 is configured as a sock/mitten similar to the wound/bandage protector 20 in FIG. 2(*a*). The wound/bandage protector 30 has a body 31 that has a first end 31A that is open and a second end 31B that is closed. However, the body 21 of the wound/bandage protector 20 has a uniform circumference from the open end 21A to the closed end 21B and a panel 22, which has a uniform width. In contrast, the body 31 of the wound/bandage protector30 is tapered from the open end 31A to the closed end 31B so that one end is larger than the other, and a panel 32 is also tapered. Alternatively, the panel 32 may also have a uniform width, regardless of the shape or circumference of the body 31. The body 31 and the panel 32 are otherwise similarly configured to the body 21 and the panel 22.

The body 31 has an external non-wound facing surface and an internal wound-facing surface. Attached to the external non-wound facing surface of the body 31 proximate to the first end 31A is a fastening strap 33A. The fastening strap 33A has a first strap part 33, a second strap part 37, a portion 36 of the second strap part 37, a first attachment region 34 and a second attachment region 35 that are configured similar to the corresponding components of the fastening strap 23A in FIG. 2(*a*).

FIG. 2(*b*) illustrates a first alternative embodiment of a protective sheath 28 and FIG. 3(*b*) illustrates a second alternative embodiment of a protective sheath 38. Both the protective sheath 28 and the protective sheath 38 may each be used in conjunction with either the wound/bandage protector 20 or the wound/bandage protector 30. Each of the protective sheaths 28, 38 has a body 28A, 38A with an opening on a first end 38B and a second end 28C, 38C that is closed. The bodies 28A, 38A are configured to fit snugly over the exterior of the wound/bandage protector 20, 30. The bodies 28A, 38A may be comprised of a waterproof or water resistant material such as the plastic material used in Playtex® bottle liners or vinyl, or a waterproof or water resistant non-woven material, and may be configured with a plastic backing and/or with the capability of being stretchable or super stretchable. Alternatively, the bodies 28A, 38A may be comprised of a composite of materials, preferably one that will provide a waterproof or water-resistant barrier. The protective sheath 28 has a slit 29 and the protective sheath 38 has a slot 39. Both the slit 29 and the slot 39 are sized and positioned to allow the fastening strap 23A, 33A of the wound/bandage protector 20,30 to fit through so that the fastening strap 23A, 33A can extend around the outside of the sheath and secure both the wound/bandage protector 20,30 as well as the sheath to an appendage being bandaged. On the wound facing side of the fastening strap 23A, 33A may be a tacky surface, which may be comprised of a pressure sensitive adhesive, or rubberized surface, or self-adherent surface material with a corresponding self-adherent surface material on the protective sheath 28, 38. Preferably, the tacky surface of the fastening strap 23A, 33A is on the first and/or second attachment regions 24, 34 and 25, 35.

Figure 4:
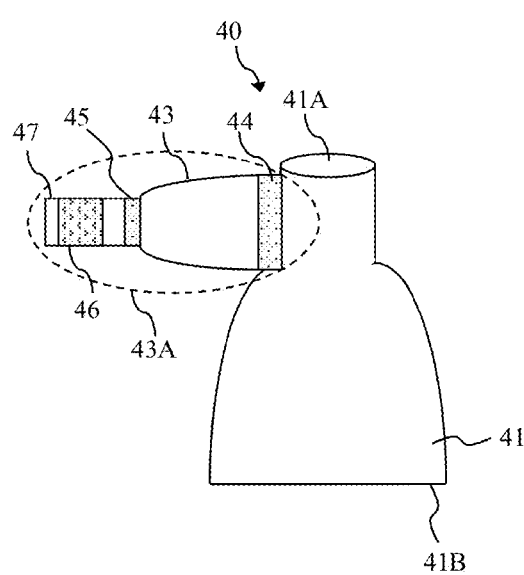
FIG. 4 is a side view of an exemplary embodiment of a bandage/wound protector according to the present invention.

FIG. 4 shows an exemplary embodiment of a wound/bandage protector 40 according to the present invention. The wound/bandage protector 40 is configured as a sock/mitten similar to the wound/bandage protector 30 in FIG. 3(a), which is similar to the wound/bandage protector 20 in FIG. 2(a). The wound/bandage protector 40 has a body 41 that has a first end 41A that is open and a second end 41B that is closed. However, the wound/bandage protector 30 has a panel 32 whereas the wound/bandage protector 40 does not have a panel.

The body 41 is otherwise similarly configured to the body 31. The body 41 has an external non-wound facing surface and an internal wound-facing surface. Attached to the external non-wound facing surface of the body 41 proximate to the first end 41A is a fastening strap 43A. The fastening strap 43A has a first strap part 43, a second strap part 47, a portion 46 of the second strap part 47 that has hook material of a hook and loop type fastener, a first attachment region 44 and a second attachment region 45 that are configured similar to the corresponding components of the fastening strap 33A in FIG. 3(a).

The wound/bandage protector 40 may be slipped onto an appendage through the wound/bandage protector opening 41A so that it covers a wound or a bandage on the appendage, or another wound/bandage protector such as the exemplary embodiments in FIGS. 2(a) and 3(a). The wound/bandage protector 40 is then secured in place by wrapping the fastening strap 43A around the outside of the wound/bandage protector 40 and affixing the portion 46 of the second strap part 47 to a loop portion of the first strap part 43, the body 41 or the loop portion of the second strap part 47.

Figure 5:
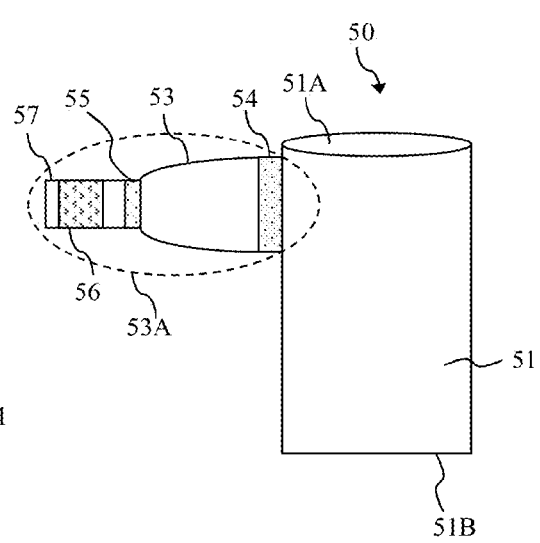
FIG. 5 is a side view of an exemplary embodiment of a bandage/wound protector according to the present invention.

FIG. 5 shows an exemplary embodiment of a wound/bandage protector 50 according to the present invention. The wound/bandage protector 50 is configured as a sock/mitten similar to the wound/bandage protector 20 in FIG. 2(a). The wound/bandage protector 50 has a body 51 that has a first end 51A that is open and a second end 51B that is closed. However, the wound/bandage protector 20 has a panel 22 whereas the wound/bandage protector 50 does not have a panel.

The body 51 is otherwise similarly configured to the body 21. The body 51 has an external non-wound facing surface and an internal wound-facing surface. Attached to the external non-wound facing surface of the body 51 proximate to the first end 51A is a fastening strap 53A. The fastening strap 53A has a first strap part 53, a second strap part 57, a portion 56 of the second strap part 57, a first attachment region 54 and a second attachment region 55 that are configured similar to the corresponding components of the fastening strap 23A in FIG. 2(a).

The wound/bandage protector 50 may be slipped onto an appendage through the wound/bandage protector opening 51A so that it covers a wound or a bandage on the appendage, or another wound/bandage protector such as the exemplary embodiments in FIGS. 2(a) and 3(a), and the wound/bandage protector 50 is then secured in place by wrapping the fastening strap 53A around the outside of the wound/bandage protector 50 and affixing the portion 56 of the second strap part 57 to the loop portion of the first strap part 53, the body 51 or the loop portion of the second strap part 57.

FIGS. 6(a)-6(c) are, respectively, a top non-wound-facing view, a bottom wound facing view, and a cross-sectional side view taken along the line II-IF of a bandage/wound protector 60 according to the present invention. The exemplary embodiment of the wound/bandage protector 60 has a body portion 61 that is configured as a wrap which may be comprised of super-stretch material similar to the super-stretch material used in the body 21, 31 of the bandage mittens/socks 20, 30. The body portion 61 is configured to act as a loop portion of a hook and loop type fastener on both the bottom wound-facing side of the wound/bandage protector 60 and the top non-wound facing side of the wound/bandage protector 60. The body portion 61 has a length that runs from a first end 61A to a second end 61B. The stretchable material of the body portion 61 at least provides such stretching capacity in a manner that allows the length of the body portion 61 to vary. The stretchable material of the body portion 61 may, alternatively, provide such stretching capacity that allows both the length of the body portion 61 as well as a width of the body portion 61 which is perpendicular to the length of the body portion 61 to vary.

A gauze port 62A is positioned on or integrated into the body portion 61 proximal to the first end of the body portion 61A. The gauze port 62A is an area where a gauze pad 69 may be attached or removably attached to the wound-facing side of the body portion 61. The gauze port 62A may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, both the gauze port 62A and the gauze pad 69 may have a low tack adhesive, such as a low tack silicone adhesive. The low tack adhesive may be on the entire non-wound facing side of the gauze pad 69, or may be just on a portion of the non-wound facing side of the gauze pad 69. Another possibility is that the surface of the gauze port 62A may be comprised of an adhesive that allows for the permanent attachment of the gauze pad 69. The gauze port 62A may be used to attach different sized gauze pads 69 as well as to periodically replace the gauze pad 69 in the bandage/wound protector 60 shown in this embodiment. The gauze port 62A may be sized and/or configured so as to attach to all, a substantial portion, or a small portion as illustrated in the FIGS. 6(b) and 6(c), such as one side of the gauze pad 69.

In closer proximity to the first end 61A of the body portion 61 of the bandage/wound protector 60 than the gauze port 62A, is a strip 62, which may be similar in configuration to the strip 4 in the first embodiment, having one or more threads made of a rubberized material that provides a moderate amount of friction interwoven in the strip 62 in such a manner that the rubberized material threads are exposed. Alternatively, the strip 62 may be made of stretch non-slip silicone or similar, preferably latex free, material that provides a frictional surface. The non-slip silicone may be applied in a continuous or discontinuous manner to form the strip 62. Preferably, the amount of friction provided by the frictional surface of the strip 62 should be one that does not cause discomfort when the bandage/wound protector 60 is worn. The strip 62 could be configured so that it is not stretchable in either one or both of the length or the width directions. The strip 62 may be provided along the top non-wound facing side of the bandage/wound protector 60 and/or the bottom wound facing side of the bandage/wound protector 60. Moreover, the strip 62 may extend around sides of the bandage/wound protector 60 and along both the top non-wound facing side of the bandage/wound protector 60 and the bottom wound facing side of the bandage/wound protector 60 so as to form an annular shape.

An end region 63A of the body portion 61 extends from the strip 62 to the first end of the body portion 61. On the end region 63A of the first end of the body portion 61A, although not necessarily on the entire end region 63A, is a first-catch fastening surface 63 on the top non-wound-facing side of the bandage/wound protector 60. The first end of the body portion 61A may be curved as shown in FIGS. 4(a) and 4(b) or straight or any other configuration.

Attached to the second end of the body portion 61B are two fastening straps 64A. Each of the fastening straps 64A may be comprised of two parts. A first strap part 64 is attached to the second end of the wound/bandage protector body portion 61B and is made out of a super-stretch material which may be adapted to function as a loop portion of a hook and loop type fastener on both the top non-wound facing side and the bottom wound-facing side of the bandage/wound protector 60. The super-stretch material of the first strap part 64 preferably provides a stretching resistance that is greater than the stretching resistance of the body portion 61. The first strap part 64 may be attached to the second end of the wound/bandage protector body portion 61B via an attachment region 65 which is preferably configured as a dead zone to provide no stretch. The attachment region 65 may be comprised of a composite of the material of the first strap part 64 and the body portion 61 of the wound/bandage protector 60 and may be attached by a punch and melt heat seal. Alternatively, the first strap part 64 is directly attached to the body portion 61 without an attachment region 65 intervening therebetween.

A second strap part 68 is attached to the first strap part 64 via an attachment region 66. The attachment region 66 is preferably configured as a dead zone to provide no stretch and may be comprised of a composite of the material of the first strap part 64 and the second strap part 68 and may be attached by a punch and melt heat seal. The second strap part 68 has a portion 67, which has a hook portion of a hook and loop type fastener on the bottom wound-facing side of each of the fastening straps 64A. Alternatively, the second strap part 68 is directly attached to the first strap part 64 without an attachment region 66 intervening therebetween. There may be a spacing 64B between inner sides of the two fastening straps 64A at the second end of the wound/bandage protector body portion 61B. The shape of the inner sides of the two fastening straps 64A may be comprised of an arc, an arc combined with a straight line, an angled line, or any other embodiment which would allow for a distance between the two inner sides of the two fastening straps 64A. The magnitude of the spacing 64B may increase along a length of the fastening straps 64A running from the first strap part 64 to the second strap part 68. The two fastening straps 64A have lengths 64C running from the second end of the wound/bandage protector body portion 61B to the second strap part 68 which may run parallel to each other. The outer sides of the two fastening straps 64A may run parallel to each other and may continue the straight lines formed by the sides of the body portion 61 of the wound/bandage protector 60.

Figure 31:
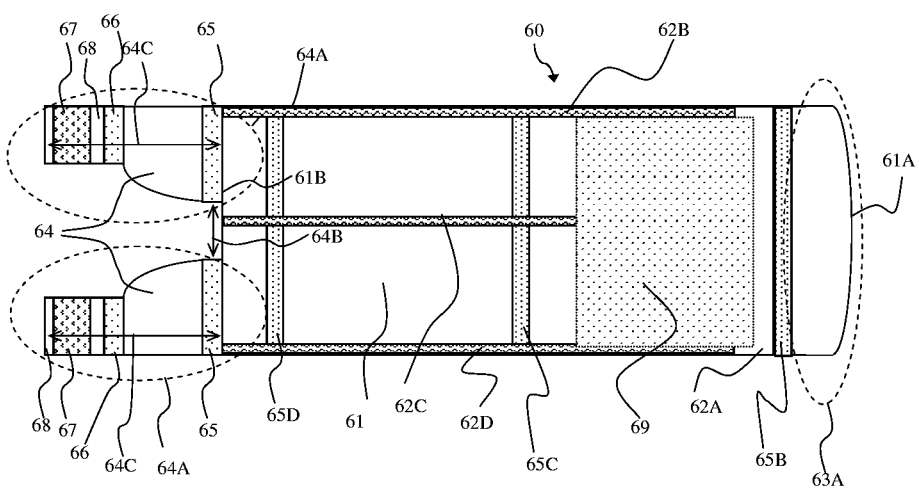
FIG. 31 is an alternative bottom wound facing side view of the exemplary embodiment of the bandage/wound protector illustrated in FIG. 6(a).

FIG. 31 shows an alternative exemplary configuration of a bottom view of the wound/bandage protector 60 according to the present invention. In this configuration, instead of the vertical strip 62, there may be a horizontal strip 62B along or proximal to an upper edge of the wound/bandage protector 60, there may be a horizontal strip 62D along or proximal to a lower edge of the wound/bandage protector 60, and there may be a horizontal strip 62C at another position between the strips 62B and 62D of the wound/bandage protector 60. There may also be any combination of these strips, i.e. only strips 62B and 62D, or 62B and 62C, or 62C and 62D, or any one of the strips 62B, 62C or 62D. In an alternative embodiment not shown in the figure, there may be one or more vertical strips along the bottom wound-facing side of wound/bandage 60 rather than horizontal strips. In another alternative embodiment not shown in the figure, rather than vertical or horizontal strips, the entire wound-facing side of the body portion 61 may be provided with a low tack non-slip silicone coating or similar material. According to this exemplary embodiment, there may be a dead zone 65B at or proximal to the first end 61A, there may be a dead zone 65D at or proximal to the second end 61B, and there may be a dead zone 65C preferably at or proximal to the middle of the body portion 61 or at some other position between the dead zone 65B and the dead zone 65D. Alternatively, instead of or in addition to the strips 62B, 62C and 62D, the dead zones 65B, 65C and 65D may be configured as strips as well.

FIGS. 7(a)-7(c) are, respectively, a top non-wound-facing view, a bottom wound facing view, and a cross-sectional side view taken along the line III-III' of a bandage/wound protector 70 according to the present invention. The exemplary embodiment of the wound/bandage protector 70 has a body portion 71 that is configured as a wrap which may be comprised of super-stretch material similar to the super-stretch material used in the body 21, 31 of the bandage mittens/socks 20, 30. The body portion 71 is configured to act as a loop portion of a hook and loop type fastener on both the bottom wound-facing side of the wound/bandage protector 70 and the top non-wound facing side of the wound/bandage protector 70. The body portion 71 has a length that runs from a first end 71A to a second end 71B. The stretchable material of the body portion 71 at least provides such stretching capacity in a manner that allows the length of the body portion 71 to vary. The stretchable material of the body portion 71 may, alternatively, provide such stretching capacity that allows both the length of the body portion 71 as well as a width of the body portion 71 which is perpendicular to the length of the body portion 71 to vary.

A gauze port 72A is positioned on or integrated into the body portion 71 proximal to the first end 71A of the body portion 71. The gauze port 72A is an area where a gauze pad 79 may be attached or removably attached to the wound-facing side of the body portion 71. The gauze port 72A may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze port 72A may be comprised of an adhesive that allows for the permanent attachment of the gauze pad 79. The gauze port 72A may be used to attach different sized gauze pads 79 as well as to periodically replace the gauze pad 79 in the bandage/wound protector 70 shown in this embodiment. The gauze port 72A may be sized and or configured so as to attach to all, a substantial portion, or a small portion such as one side of the gauze pad 79.

In closer proximity to the first end 71A of the body portion 71 of the bandage/wound protector 70 than the gauze port 72A, is a strip 72, which may be similar in configuration to the strip 4 in the first embodiment, having one or more threads made of a rubberized material that provides a moderate amount of friction interwoven in the strip 72 in such a manner that the rubberized material threads are exposed. Alternatively, the strip 72 may be made of other material that provides a frictional surface. Preferably, the amount of friction provided by the frictional surface of the strip 72 should be one that does not cause discomfort when the bandage/wound protector 70 is worn. The strip 72 could be configured so that it is not stretchable in either one or both of the length or the width directions. The strip 72 may be provided along the top non-wound facing side of the bandage/wound protector 70 and/or the bottom wound facing side of the bandage/wound protector 70. Moreover, the strip 72 may extend around sides of the bandage/wound protector 70 and along both the top non-wound facing side of the bandage/wound protector 70 and the bottom wound facing side of the bandage/wound protector 70 so as to form an annular shape.

An end region 73A of the body portion 71 extends from the strip 72 to the first end 71A of the body portion 71. A portion of the end region 73A may be tapered so as to provide a gradual diminution in the width of the body portion 71 toward the first end 71A. A tab 75 extends from the first end 71A of the body portion 71. The tab 75 may be centered along the outer edge of the first end 71A. On the tab 75 is a first catch fastening surface 73 on the top non-wound-facing side of the bandage/wound protector 70. The first catch fastening surface 73 may also extend onto the end region 73A.

On the second end of the body portion 71B are two fastening straps 74. The two fastening straps 74 are a continuation of the same piece of super-stretch material as the body portion 71. There may be a spacing 74B between inner sides of the two fastening straps 74A at the second end of the wound/bandage protector body portion 71B. The shape of the inner sides of the two fastening straps 74 may be an angled line as shown in FIGS. 5(a) & 5(b), an arc, an arc combined with a straight line, or any other configuration which would allow for a distance between the two inner sides of the two fastening straps 74. The magnitude of the spacing 74B may increase along a length of the fastening straps 74. The two fastening straps 74 have lengths 74C running from the second end of the wound/bandage protector body portion 71B to the second strap part 78 which may run parallel to each other. Outer sides of the two fastening straps 74A may run parallel to each other and may continue straight lines formed by the sides of the body portion 71 of the wound/bandage protector 70, as shown in FIGS. 5(a) & 5(b). Alternatively, the outer sides of the two fastening straps 74 may assume a shape that tapers inwardly, toward the inner sides of the fastening straps 74A, or outwardly, away from the inner sides of the fastening straps 74A. An end portion 77 of each of the two fastening straps 74 has a hook type material of a hook and loop type fastener on the bottom wound-facing side of the wound/bandage protector 70.

FIGS. 8(a)-8(c) are, respectively, a top non-wound-facing view, a bottom wound facing view, and a cross-sectional side view taken along the line IV-IV' of a bandage/wound protector 80 according to the present invention. The exemplary embodiment of the wound/bandage protector 80 has a body portion 81 that is configured as a wrap which may be comprised of super-stretch material similar to the super-stretch material used in the body 21, 31 of the bandage mittens/socks 20, 30. The body portion 81 is configured to act as a loop portion of a type fastener on both the bottom wound-facing side of the wound/bandage protector 80 and the top non-wound facing side of the wound/bandage protector 80. The body portion 81 has a length that runs from a first end 81A to a second end 81B. The stretchable material of the body portion 81 at least provides such stretching capacity in a manner that allows the length of the body portion 81 to vary. The stretchable material of the body portion 81 may, alternatively, provide such stretching capacity that allows both the length of the body portion 81 as well as a width of the body portion 81 which is perpendicular to the length of the body portion 81 to vary.

A gauze port 82A is positioned on or integrated into the body portion 81 proximal to the first end 81A of the body portion 81. The gauze port 82A is an area where a portion of a gauze pad 89 may be attached or removably attached to the wound-facing side of the body portion 81. The gauze port 82A may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze port 82A may be comprised of an adhesive that allows for the permanent attachment of the gauze pad 89. The gauze port 82A may be used to attach different sized gauze pads 89 as well as to periodically replace the gauze pad 89 in the bandage/wound protector 80 shown in this embodiment. The gauze port 82A may be sized and or configured so as to attach to all, a substantial portion, or a small portion such as one side of the gauze pad 89.

In closer proximity to the first end 81A of the body portion 81 of the bandage/wound protector 80 than the gauze port 82A, is a strip 82, which may be similar in configuration to the strip 4 in the first embodiment, having one or more threads made of a rubberized material that provides a moderate amount of friction interwoven in the strip 82 in such a manner that the rubberized material threads are exposed. Alternatively, the strip 82 may be made of other material that provides a frictional surface. Preferably, the amount of friction provided by the frictional surface of the strip 82 should be one that does not cause discomfort when the bandage/wound protector 80 is worn. The strip 82 could be configured so that it is not stretchable in either one or both of the length or the width directions. The strip 82 may be provided along the top non-wound facing side of the bandage/wound protector 80 and/or the bottom wound facing side of the bandage/wound protector 80. Moreover, the strip 82 may extend around sides of the bandage/wound protector 80 and along both the top non-wound facing side of the bandage/wound protector 80 and the bottom wound facing side of the bandage/wound protector 80 so as to form an annular shape.

An end region 83A of the body portion 81 extends from the strip 82 to the first end 81A of the body portion 81. A portion of the end region 83A may be tapered so as to provide a gradual diminution in the width of the body portion 81 toward the first end 81A. A tab 85 extends from the first end 81A of the body portion 81. The tab 85 may be centered along the outer edge of the first end 81A. On the tab 85 is a first catch fastening surface 83 on the top non-wound-facing side of the bandage/wound protector 80. The first catch fastening surface 83 may also extend onto the end region 83A.

A second end region 88 extends along the body portion 81 from a point along the length of the body portion 81 that is proximal to the second end 81B of the body portion 81, to the second end 81B. A portion of the end region 88 may be tapered so as to provide a gradual diminution in the width of the body portion 81 toward the second end 81B. On the second end region 88, although not necessarily on the entire second end region 88, is a fastening portion 84 that can engage and hold fast to the body portion 81 on the top non-wound facing side of the wound/bandage protector 80, or a portion thereof. The fastening portion 84 may be made of hook type material of a hook and loop fastener provided on the bottom wound-facing side of the wound/bandage protector 80.

FIGS. 9(a)-9(c) are, respectively, a top non-wound-facing view, a bottom wound facing view, and a cross-sectional side view taken along the line V-V' of a bandage/wound protector 90 according to the present invention. The exemplary embodiment of the wound/bandage protector 90 has a body portion 91 that is configured as a wrap which may be comprised of super-stretch material similar to the super-stretch material used in the body 21, 31 of the bandage mittens/socks 20, 30. The body portion 91 is configured to act as a loop portion of a hook and loop type fastener on both the bottom wound-facing side of the wound/bandage protector 90 and the top non-wound facing side of the wound/bandage protector 90. The body portion 91 has a length that runs from a first end 91A to a second end 91B. The stretchable material of the body portion 91 at least provides such stretching capacity in a manner that allows the length of the body portion 91 to vary. The stretchable material of the body portion 91 may, alternatively, provide such stretching capacity that allows both the length of the body portion 91 as well as a width of the body portion 91 which is perpendicular to the length of the body portion 91 to vary.

A gauze panel 92A is positioned on or integrated into the body portion 91 proximal to the first end 91A of the body portion 91. The gauze panel 92A is an area where all or substantially all of a gauze pad 99 may be attached or removably attached to the wound-facing side of the body portion 91. The gauze panel 92A may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze panel 92A may be comprised of an adhesive that allows for the permanent attachment of the gauze pad 99. The gauze panel 92A may be used to attach different sized gauze pads 99 as well as to periodically replace the gauze pad 99 in the bandage/wound protector 90 shown in this embodiment.

In closer proximity to the first end 91A of the body portion 91 of the bandage/wound protector 90 than the gauze panel 92A, may be a strip 92, which may be similar in configuration to the strip 4 in the first embodiment, having one or more threads made of a rubberized material that provides a moderate amount of friction interwoven in the strip 92 in such a manner that the rubberized material threads are exposed. Alternatively, the strip 92 may be made of other material that provides a frictional surface. Preferably, the amount of friction provided by the frictional surface of the strip 92 should be one that does not cause discomfort when the bandage/wound protector 90 is worn. The strip 92 could be configured so that it is not stretchable in either one or both of the length or the width directions. The strip 92 may be provided along the top non-wound facing side of the bandage/wound protector 90 and/or the bottom wound facing side of the bandage/wound protector 90. Moreover, the strip 92 may extend around sides of the bandage/wound protector 90 and along both the top non-wound facing side of the bandage/wound protector 90 and the bottom wound facing side of the bandage/wound protector 90 so as to form an annular shape.

An end region 93A of the body portion 91 extends from the strip 92 to the first end 91A of the body portion 91. A portion of the end region 93A may be tapered so as to provide a gradual diminution in the width of the body portion 91 toward the first end 91A. A tab 95 extends from the first end 91A of the body portion 91. The tab 95 may be centered along the outer edge of the first end 91A. On the tab 95 is a first catch fastening surface 93 on the top non-wound-facing side of the bandage/wound protector 90. The first catch fastening surface 93 may also extend onto the end region 93A.

A second end region 98 extends along the body portion 91 from a point along the length of the body portion 91 that is proximal to the second end 91B of the body portion 91, to the second end 91B. A portion of the end region 98 may be tapered so as to provide a gradual diminution in the width of the body portion 91 toward the second end 91B. On the second end region 98, although not necessarily on the entire second end region 98, is a fastening portion 94 that can engage and hold fast to the body portion 91 on the top non-wound facing side of the wound/bandage protector 90, or a portion thereof. The fastening portion 94 may be made of hook type material of a hook and loop type fastener provided on the bottom wound-facing side of the wound/bandage protector 90.

Figure 10A:
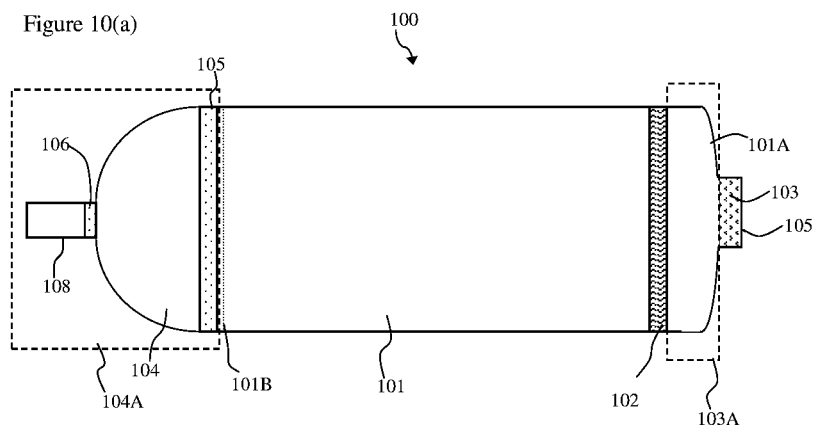
FIG. 10(*a*) is a top non-wound facing side view of a exemplary embodiment of a bandage/wound protector according to the present invention.
FIG. 10(c) is a side cross-sectional view of the exemplary embodiment of the bandage/wound protector illustrated in FIGS. 10(a) and (b) taken along the line VI-VI' in FIG. 10(b)
Figure 10B:
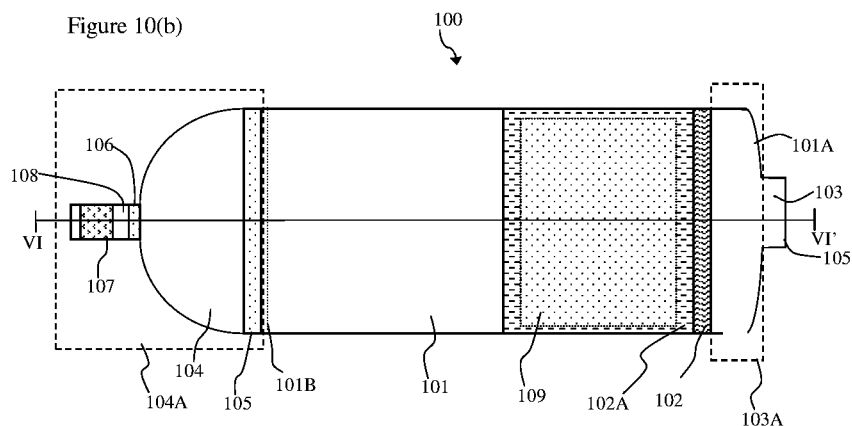
Figure 10C:
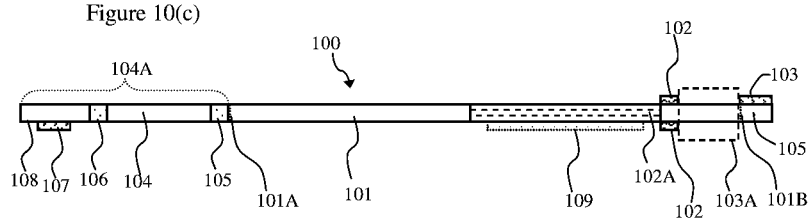

FIGS. 10(a)-10(c) are, respectively, a top non-wound-facing view, a bottom wound facing view, and a cross-sectional side view taken along the line VI-VI' of a bandage/wound protector 100 according to the present invention. The exemplary embodiment of the wound/bandage protector 100 has a body portion 101 that is configured as a wrap, which may be comprised of super-stretch material similar to the super-stretch material used in the body 21, 31 of the bandage mittens/socks 20, 30. The body portion 101 is configured to act as a loop portion of a hook and loop type fastener on both the bottom wound-facing side of the wound/bandage protector 100 and the top non-wound facing side of the wound/bandage protector 100. The body portion 101 has a length that runs from a first end 101A to a second end 101B. The stretchable material of the body portion 101 at least provides such stretching capacity in a manner that allows the length of the body portion 101 to vary. The stretchable material of the body portion 101 may, alternatively, provide such stretching capacity that allows both the length of the body portion 101 as well as a width of the body portion 101 which is perpendicular to the length of the body portion 101 to vary.

A gauze panel 102A is positioned on or integrated into the body portion 101 proximal to the first end 101A of the body portion 101. The gauze panel 102A is an area where all or substantially all of a gauze pad 109 may be attached or removably attached to the wound-facing side of the body portion 101. The gauze panel 102A may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze panel 102A may be comprised of an adhesive that allows for the permanent attachment of the gauze pad 109. The gauze panel 102A may be used to attach different sized gauze pads 109 as well as to periodically replace the gauze pad 109 in the bandage/wound protector 100 shown in this embodiment.

In closer proximity to the first end 101A of the body portion 101 of the bandage/wound protector 100 than the gauze panel 102A, may be a strip 102, which may be similar in configuration to the strip 4 in the first embodiment, having one or more threads made of a rubberized material that provides a moderate amount of friction interwoven in the strip 102 in such a manner that the rubberized material threads are exposed. Alternatively, the strip 102 may be made of other material that provides a frictional surface. Preferably, the amount of friction provided by the frictional surface of the strip 102 should be one that does not cause discomfort when the bandage/wound protector 100 is worn. The strip 102 could be configured so that it is not stretchable in either one or both of the length or the width directions. The strip 102 may be provided along the top non-wound facing side of the bandage/ wound protector 100 and/or the bottom wound facing side of the bandage/wound protector 100. Moreover, the strip 102 may extend around sides of the bandage/wound protector 100 and along both the top non-wound facing side of the bandage/wound protector 100 and the bottom wound facing side of the bandage/wound protector 100 so as to form an annular shape.

An end region 103A of the body portion 101 extends from the strip 102 to the first end 101A of the body portion 101. A portion of the end region 103A may be tapered so as to provide a gradual diminution in the width of the body portion 101 toward the first end 101A. A tab 105 extends from the first end 101A of the body portion 101. The tab 105 may be centered along the outer edge of the first end 101A. On the tab 105 is a first catch fastening surface 103 on the top non-wound-facing side of the bandage/wound protector 100. The first catch fastening surface 103 may also extend onto the end region 103A.

Attached to the second end of the body portion 101B is a fastening strap 104A. The fastening strap 104A may be comprised of two parts. A first strap part 104 is attached to the second end of the wound/bandage protector body portion 101B and is made out of a super-stretch material which may be adapted to function as a loop portion of a hook and loop type fastener on both the top non-wound facing side and the bottom wound-facing side of the bandage/wound protector 100. The super-stretch material of the first strap part 104 preferably provides a stretching resistance that is greater than the stretching resistance of the body portion 101. The first strap part 104 may be attached to the second end of the wound/bandage protector body portion 101B via an attachment region 105 which is preferably configured to provide no stretch. The attachment region 105 may be comprised of a composite of the material of the first strap part 104 and the body portion 101 of the wound/bandage protector 100 and may be attached by a punch and melt heat seal. Alternatively, the first strap part 104 is directly attached to the body portion 101 without an attachment region 105 intervening therebetween. A second strap part 108 is attached to the first strap part 104 via an attachment region 106. The attachment region 106 may be comprised of a composite of the material of the first strap part 104 and the second strap part 108 and may be attached by a punch and melt heat seal. The second strap part 108 has a portion 107 which includes a hook type material of a hook and loop type fastener on the bottom wound-facing side of the fastening strap 104A. Alternatively, the second strap part 108 is directly attached to the first strap part 104 without an attachment region 106 intervening therebetween.

Figure 11A:
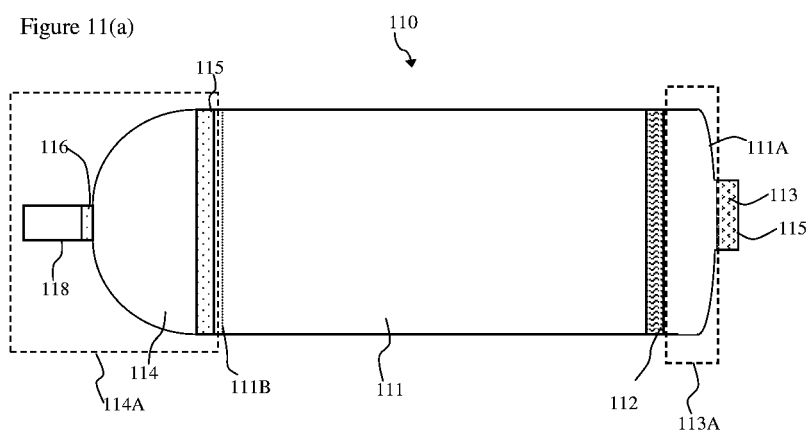
FIG. 11(a) is a top non-wound facing side view of an exemplary embodiment of a bandage/wound protector according to the present invention.
Figure 11B:
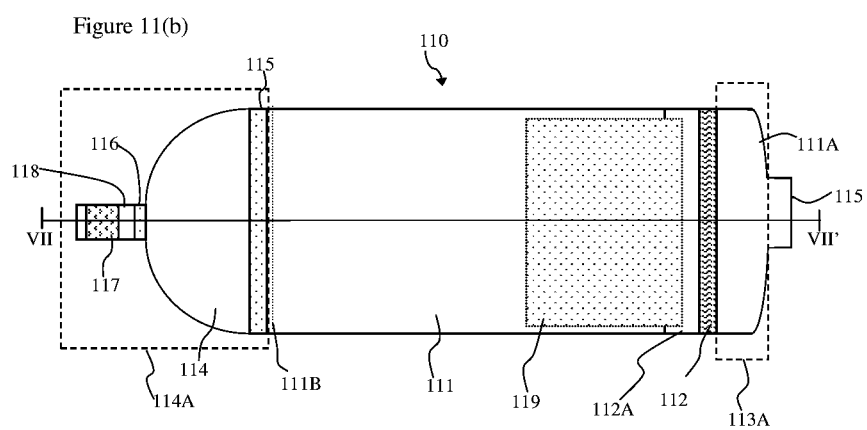
FIG. 11(b) is a bottom wound facing side view of the exemplary embodiment of the bandage/wound protector illustrated in FIG. 11(a)
Figure 11C:
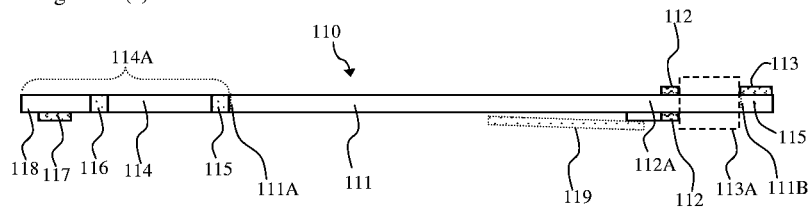
FIG. 11(c) is a side cross-sectional view of the exemplary embodiment of the bandage/wound protector illustrated in FIGS. 11(a) and (b) taken along the line VII-VII' in FIG. 11(b)
Figure 23A:
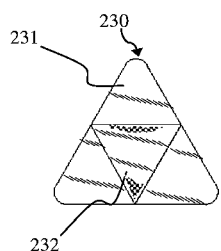
FIG. 23(a) shows a bottom wound-facing side of an exemplary embodiment of a "triangular gauze" adhesive bandage according to the present invention.
Figure 23B:
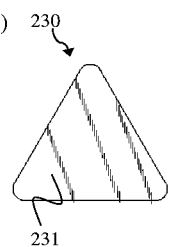
FIG. 23(b) shows a top non-wound-facing side of the exemplary embodiment of the "triangular gauze" adhesive bandage illustrated in FIG. 23(a)
Figure 23C:
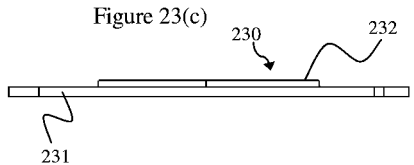
FIG. 23(c) shows a first side view of the exemplary embodiment of the "triangular gauze" adhesive bandage illustrated in FIGS. 23(a) and (b)
Figure 23D:
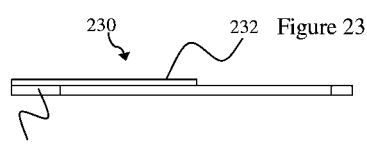
FIG. 23(d) shows a second side view of the exemplary embodiment of the "triangular gauze" adhesive bandage illustrated in FIGS. 23(a) and (b)
Figure 23E:
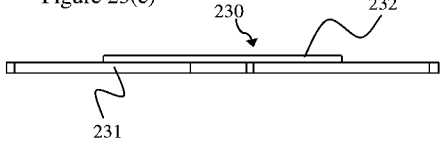
FIG. 23(e) shows a first end view of the exemplary embodiment of the "triangular gauze" adhesive bandage illustrated in FIGS. 23(a) and (b)
Figure 23F:
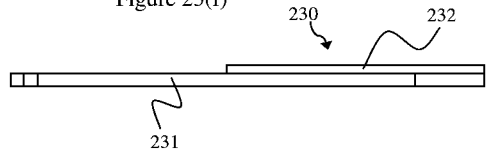
FIG. 23(f) shows a second end view of the exemplary embodiment of the "triangular gauze" adhesive bandage illustrated in FIGS. 23(a) and (b)
Figure 23G:
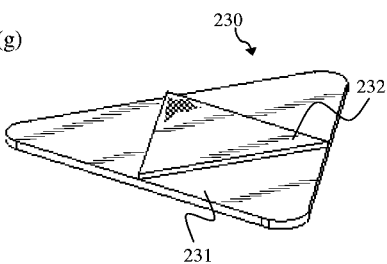
FIG. 23(g) shows a perspective view of the exemplary embodiment of the "triangular gauze" adhesive bandage illustrated in FIGS. 23(a) and (b)

FIGS. 11(a)-11(c) are, respectively, a top non-wound-facing view, a bottom wound facing view, and a cross-sectional side view taken along the line VII-VII' of a bandage/wound protector 110 according to the present invention. The exemplary embodiment of the wound/bandage protector 110 has a body portion 111 that is configured as a wrap, which may be comprised of super-stretch material similar to the super-stretch material used in the body 21, 31 of the bandage mittens/socks 20, 30. The body portion 111 is configured to act as a loop portion of a hook and loop type fastener on both the bottom wound-facing side of the wound/bandage protector 110 and the top non-wound facing side of the wound/bandage protector 110. The body portion 111 has a length that runs from a first end 111A to a second end 111B. The stretchable material of the body portion 111 at least provides such stretching capacity in a manner that allows the length of the body portion 111 to vary. The stretchable material of the body portion 111 may, alternatively, provide such stretching capacity that allows both the length of the body portion 111 as well as a width of the body portion 111 which is perpendicular to the length of the body portion 111 to vary.

A gauze port 112A is attached to the body portion 111 proximal to the first end 111A of the body portion 111. The gauze port 112A is an area where a portion of a gauze pad 119 may be attached or removably attached to the wound-facing side of the body portion 111. The gauze port 112A may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze port 112A may be comprised of an adhesive that allows for the permanent attachment of the gauze pad 119. The gauze port 112A may be used to attach different sized gauze pads 119 as well as to periodically replace the gauze pad 119 in the bandage/wound protector 110 shown in this embodiment. The gauze port 112A may be sized and or configured so as to attach to all, a substantial portion, or a small portion such as one side of the gauze pad 119.

In closer proximity to the first end 111A of the body portion 111 of the bandage/wound protector 110 than the gauze port 112A, may be a strip 112, which may be similar in configuration to the strip 4 in the first embodiment, having one or more threads made of a rubberized material that provides a moderate amount of friction interwoven in the strip 112 in such a manner that the rubberized material threads are exposed. Alternatively, the strip 112 may be made of other material that provides a frictional surface. Preferably, the amount of friction provided by the frictional surface of the strip 112 should be one that does not cause discomfort when the bandage/wound protector 110 is worn. The strip 112 could be configured so that it is not stretchable in either one or both of the length or the width directions. The strip 112 may be provided along the top non-wound facing side of the bandage/wound protector 110 and/or the bottom wound facing side of the bandage/wound protector 110. Moreover, the strip 112 may extend around sides of the bandage/wound protector 110 and along both the top non-wound facing side of the bandage/wound protector 110 and the bottom wound facing side of the bandage/wound protector 110 so as to form an annular shape.

An end region 113A of the body portion 111 extends from the strip 112 to the first end 111A of the body portion 111. A portion of the end region 113A may be tapered so as to provide a gradual diminution in the width of the body portion 111 toward the first end 111A. A tab 115 extends from the first end 111A of the body portion 111. The tab 115 may be centered along the outer edge of the first end 111A. On the tab 115 is a first catch fastening surface 113 on the top non-wound-facing side of the bandage/wound protector 110. The first catch fastening surface 113 may also extend onto the end region 113A.

Attached to the second end of the body portion 111B is a fastening strap 114A. The fastening strap 114A may be comprised of two parts. A first strap part 114 is attached to the second end of the wound/bandage protector body portion 111B and is made out of a super-stretch material which may be adapted to function as a loop portion of a hook and loop type fastener on both the top non-wound facing side and the bottom wound-facing side of the bandage/wound protector 110. The super-stretch material of the first strap part 114 preferably provides a stretching resistance that is greater than the stretching resistance of the body portion 111. The first strap part 114 may be attached to the second end of the wound/bandage protector body portion 111B via an attachment region 115 which is preferably configured to provide no stretch. The attachment region 115 may be comprised of a composite of the material of the first strap part 114 and the body portion 111 of the wound/bandage protector 110 and may be attached by a punch and melt heat seal. Alternatively, the first strap part 114 is directly attached to the body portion 111 without an attachment region 115 intervening therebetween. A second strap part 118 is attached to the first strap part 114 via an attachment region 116. The attachment region 116 may be comprised of a composite of the material of the first strap part 114 and the second strap part 118 and may be attached by a punch and melt heat seal. The second strap part 118 has a portion 117 which includes a hook type material of a hook and loop fastener on the bottom wound-facing side of the fastening strap 114A. Alternatively, the second strap part 118 is directly attached to the first strap part 114 without an attachment region 116 intervening therebetween.

In certain situations, it may be preferable to apply an adhesive bandage to a wound, particularly on joints, whose constant movement may cause the gauze to move. In those situations, according to the present invention, a "diamond gauze", "triangle gauze" or "stretchable gauze" adhesive bandage, as discussed below, are preferably utilized as they have been found to have advantages over other bandages known in the art. One of the advantages of the "diamond gauze", "triangle gauze" and "stretchable gauze" bandages is that they can provide superior adherence and conformability to a wound area with a maximal area of gauze, particularly for wounds on joints. The "diamond gauze", "triangle gauze", and "stretchable gauze" adhesive bandages may be used alone or in conjunction with the super-stretch tube in FIG. 1 or a bandage wound/protector such as those shown in FIGS. 2 through 11, preferably without the gauze pad which may be shown as an alternative in those figures. In addition, the "diamond gauze", "triangle gauze" and "stretchable gauze" configurations discussed below may be integrated with a bandage wound/protector such as those shown in FIGS. 2 through 11 without the use of a separate adhesive bandage. Moreover, the "diamond gauze" and "triangle gauze" bandages may concurrently be configured as "stretchable gauze" bandages. A "stretchable gauze" bandage is any bandage with a stretchable body portion and a stretchable gauze pad affixed to the wound-facing side of the body portion. The body portion may have adhesive on at least a portion of a wound facing side or, alternatively, the body portion may include self adherent material, such as the nonwoven laminate used in 3M™ Coban™ Self-Adherent Wrap.

FIGS. 12(a)-12(f) are, respectively, a bottom wound-facing view, a top non-wound facing view, two side views and two perspective views of an exemplary embodiment of a "diamond gauze" adhesive bandage 120 according to the present invention. The "diamond gauze" adhesive bandage 120 has a body portion 121 in a square shape, preferably with rounded corners, which may be made of any suitable material, preferably a stretchable and breathable material, which is known in the art to be used for adhesive bandages. A gauze pad 122 is attached to the wound-facing side of the body portion 121 of the "diamond gauze" adhesive bandage 120. The gauze pad 122 is a square shape. Alternatively, the gauze pad 122 may be configured in the shape of a diamond or rhombus. The corners of the gauze pad 122 may be rounded and the sides of the gauze pad need 122 need not be perfectly straight. For example, a side of the gauze pad 122 may be convex or concave curve or a wavy line. Corners of the gauze pad 122 are offset from the corners of the body portion 121 of the "diamond gauze" adhesive bandage 120 such that the sides of the gauze pad 122 are not parallel to the sides of the body portion 121 of the "diamond gauze" adhesive bandage 120. In other words, each of the corners of the gauze pad 122 are oriented towards a different length tangent or width tangent of the "diamond gauze" adhesive bandage 120. In regard to the "diamond gauze" bandages disclosed herein, the length and width tangents may be defined by the edges of the body portion 121 relative to the wound facing side of the body portion. Thus, where the body portion is square or rectangular the length and width tangents are not explicitly defined as they are the edges of the body portion itself. Similarly, in exemplary embodiments where the body portion has a different shape but one of the length or width tangents is contiguous with the tangent, the tangent line is not explicitly defined. Otherwise, the length and width tangents are a set of explicitly defined tangents that intersect with the edges of the bandage and form a square or rectangular shape. Also note that the terms length and width with respect to such tangents does not necessarily indicate that length tangents are longer than width tangents. Preferably, the gauze pad 122 is oriented so that each of the sides of the gauze pad 122 are parallel to a hypotenuse of an isosceles right triangle formed with two contiguous sides of the body portion 121 of the "diamond gauze" adhesive bandage 120. The gauze pad 122 may have the same center point as the body portion 121, and/or each of the corners of the gauze pad 122 may be oriented toward a mid-point of one of the sides of body portion 121. The size of the gauze pad 122 is such that the corners of the gauze pad 122 do not reach the sides of the body portion 121 of the "diamond gauze" adhesive bandage 120. The gauze pad 122 may be sized and positioned so as to substantially define four equal quadrants on the wound facing side of the body portion 121. The bottom wound-facing side of the body portion 121 of the "diamond gauze" adhesive bandage 120 may have adhesive as those used for bandages in the art. The adhesive may be applied to all or part of the bottom wound-facing side of the body portion 121 of the "diamond gauze" adhesive bandage 120. The gauze pad 122 may or may not be affixed to the body portion 121 of the "diamond gauze" adhesive bandage 120 via the same adhesive as that which is used to affix the "diamond gauze" adhesive bandage 120 to a patient.

FIGS. 13(a)-13(f) are, respectively, a bottom wound-facing view, a top non-wound facing view, two side views and two perspective views of an exemplary embodiment of a "diamond gauze" adhesive bandage 130 according to the present invention. In contrast to the exemplary embodiment shown in FIGS. 12(a)-12(f), the size of the gauze pad 132 in the "diamond gauze" adhesive bandage 130 is such that the corners of the gauze pad 132 reach the sides of a body portion 131 of the adhesive bandage 130. The gauze pad 132 may be sized and positioned so as to define four equal quadrants on the wound facing side of the body portion 131. In all other respects the configuration of the adhesive bandage 130 is comparable to the configuration of the adhesive bandage 120.

FIGS. 14(a) through 14(e) are, respectively, a bottom wound-facing view, a top non-wound facing view, two side views and one perspective view of an exemplary embodiment of a "diamond gauze" adhesive bandage 140 according to the present invention. In the "diamond gauze" adhesive bandage 140, a body portion 141 of the adhesive bandage 140 has a rectangular shape, preferably with rounded corners. A gauze pad 142 is oriented with respect to the body portion 141 of the "diamond gauze" adhesive bandage 140 such that the sides of the gauze pad 142 are not parallel to the sides of the body portion 141 of the "diamond gauze" adhesive bandage 140. In such a case, the gauze pad 142 may be sized so that two opposing corners may touch two opposing sides of the body portion 141 of the adhesive bandage 140 while the remaining corners of the gauze pad 142 do not touch the remaining sides of the body portion 141 of the adhesive bandage 140. The gauze pad 142 is configured in the shape of a square. The gauze pad 142 may have the same center point as the body portion 141 and/or each of the corners of the gauze pad 142 may be oriented toward a mid-point of one of the sides of body portion 141. As shown in FIGS. 18(a)-(e), for a "diamond gauze" adhesive bandage 180 with a rectangular shaped body portion 181, the gauze pad 182 may also be configured in the shape of a diamond. Moreover, for any of "diamond gauze" bandages, according to the present invention, the gauze pad may be configured in the shape of a square, diamond or rhombus. Furthermore, for any of the "diamond gauze" bandages, according to the present invention, the gauze pad may be sized and positioned so that some or all of the gauze pad corners extend to the edges of the body portion.

FIGS. 15(a)-15(e) are, respectively, a bottom wound-facing view, a top non-wound facing view, two side views and one perspective view of another exemplary embodiment of a "diamond gauze" adhesive bandage 150 according to the present invention. The body portion 151 of the "diamond gauze" adhesive bandage 150 is an oval shape. The gauze pad 152 is oriented with respect to the body portion 151 of the "diamond gauze" adhesive bandage 150 such that the sides of the gauze pad 152 are not parallel to the sides of a rectangle formed by tangents 159A, 159B, 159C, and 159D of the body portion 151 of the "diamond gauze" adhesive bandage 150. The tangents form a rectangular or square area whose length and width are defined by tangents to the edges of the bandage. The gauze pad 152 may have the same center point as the body portion 151 and/or each of the corners of the gauze pad 152 may be oriented toward a mid-point of one of the tangents 159A, 159B, 159C, and 159D.

FIGS. 16(a)-16(e) are, respectively, a bottom wound-facing view, a top non-wound facing view, two side views and one perspective view of another exemplary embodiment of a "diamond gauze" adhesive bandage 160 according to the present invention. The body portion 161 of the "diamond gauze" adhesive bandage 160 is an almond shape which among other bandaging uses may be particularly useful for bandaging a finger tip or similar appendage. The gauze pad 162 is oriented with respect to the body portion 161 of the "diamond gauze" adhesive bandage 160 such that the sides of the gauze pad 162 are not parallel to the sides of a rectangle formed by tangents 169A, 169B, 169C, and 169D of the body portion 161 of the "diamond gauze" adhesive bandage 160. The gauze pad 162 may have the same center point as the body portion 161 and/or each of the corners of the gauze pad 162 may be oriented toward a mid-point of one of the tangents 169A, 169B, 169C, and 169D.

FIGS. 17(a)-17(e) are, respectively, a bottom wound-facing view, a top non-wound facing view, two side views and one perspective view of another exemplary embodiment of a "diamond gauze" adhesive bandage 170 according to the present invention. The body portion 171 of the "diamond gauze" adhesive bandage 170 is an hourglass shape which among other bandaging uses may be particularly useful for bandaging a finger tip or similar appendage. The gauze pad 172 is oriented with respect to the body portion 171 of the "diamond gauze" adhesive bandage 170 such that the sides of the gauze pad 172 are not parallel to the sides of a rectangle formed by tangents 179A and 179B, and edges 179C and 179D of the body portion 171 of the "diamond gauze" adhesive bandage 170. The gauze pad 172 may have the same center point as the body portion 171, and/or each of the corners of the gauze pad 172 may be oriented toward a mid-point of one of the tangents 179A and 179B and edges 179C and 179D of the body portion 171 of the "diamond gauze" adhesive bandage 170.

FIGS. 19(a)-19(g) are, respectively, a bottom wound-facing view, a top non-wound facing view, four side views and one perspective view of another exemplary embodiment of a "diamond gauze" adhesive bandage 190 according to the present invention. The body portion 191 of the "diamond gauze" adhesive bandage 190 has a shape which among other bandaging uses may be particularly useful for bandaging a finger tip, knuckle, or similar appendage. The gauze pad 192 is oriented with respect to the body portion 191 of the "diamond gauze" adhesive bandage 190 such that the sides of the gauze pad 192 are not parallel to the sides of a rectangle formed by tangents 199A, 199B, 199C, and 199D of the body portion 191 of the "diamond gauze" adhesive bandage 190.

FIGS. 20(a)-20(g) are, respectively, a bottom wound-facing view, a top non-wound facing view, four side views and one perspective view of another exemplary embodiment of a "diamond gauze" adhesive bandage 200 according to the present invention. The body portion 201 of the "diamond gauze" adhesive bandage 200 has a shape which among other bandaging uses may be particularly useful as a finger wrap. The body portion 201 of the "diamond gauze" adhesive bandage 200 may be comprised of self-adherent material so that when it is wrapped around a finger or other appendage, a wound facing side of the bandage that is distal to the gauze pad adheres to the non-wound facing side of the body portion 201 so as to secure the wrap in place. Similarly, all the other "diamond gauze" adhesive bandages, particularly when used to wrap around an appendage, may be made of such self-adherent material. The gauze pad 202 is oriented with respect to the body portion 201 of the "diamond gauze" adhesive bandage 200 such that the sides of the gauze pad 202 are not parallel to the sides of a rectangle formed by tangents 209A, 209B, 209C, and 209D of the body portion 201 of the "diamond gauze" adhesive bandage 200. Alternatively, the "diamond gauze" adhesive bandage 200 may be used with the gauze pad 202 not oriented as a diamond shape, but rather in the standard rectangular or square orientation that parallels the length of the bandage, particularly when the adhesive bandage 200 is configured with self-adherent material or other material for the purpose of resealing the bandage.

FIGS. 21(a)-21(e) are, respectively, a bottom wound-facing view, a top non-wound facing view, two side views and one perspective view of another exemplary embodiment of a "diamond gauze" adhesive bandage 210 according to the present invention. The body portion 211 of the "diamond gauze" adhesive bandage 210 is an elongated octagonal shape. The gauze pad 212 is oriented with respect to the body portion 211 of the "diamond gauze" adhesive bandage 210 such that the sides of the gauze pad 212 are not parallel to edges 219A, 219B, 219C and 219D of the body portion 127 of the "diamond gauze" adhesive bandage 210. The gauze pad 212 may have the same center point as the body portion 211 and/or each of the corners of the gauze pad 212 may be oriented toward a mid-point of one of the edges 219A, 219B, 219C and 219D of the body portion 127 of the "diamond gauze" adhesive bandage 210. Alternatively, the body portion 211 of the "diamond gauze" adhesive bandage 210 may be an octagonal shape with eight equal sides.

According to the present invention, an alternative to the "diamond gauze" configuration of an adhesive bandage is a "triangular gauze" adhesive bandage, as discussed below. The "triangular gauze" configuration provides similar advantages to the "diamond gauze" particularly superior adherence and conformability to a wound area with a maximal area of gauze.

The "triangular gauze" configuration may be especially useful in bandaging smaller wounds.

FIGS. 22(a)-22(g) are, respectively, a bottom wound-facing view, a top non-wound facing view, four side views and one perspective view of another exemplary embodiment of a "triangular gauze" adhesive bandage 220 according to the present invention. The "triangular gauze" adhesive bandage 220 has a body portion 221 in a circular shape, which may be made of any suitable material, preferably a stretchable and breathable material, which is known in the art to be used for adhesive bandages. A gauze pad 222 is attached to the wound-facing side of the body portion 221. The gauze pad 222 is a triangular shape, preferably an equilateral triangular shape, but the gauze pad 222 may alternatively be configured as an isosceles, right or other triangular shape and may have rounded or flattened corners. The gauze pad 222 may be positioned so as to have the same center point as the body portion 221, with each of the corners of the gauze pad 222 extending to the sides of body portion 221. Alternatively, the gauze pad 222 may be sized so that the corners of the gauze pad 222 do not reach the sides of the body portion 221. The gauze pad 222 may be sized and positioned so as to substantially define three equal quadrants on the wound facing side of the body portion 221. The bottom wound-facing side of the body portion 221 of the "triangular gauze" adhesive bandage 220 may have adhesive as those used for bandages in the art. The adhesive may be applied to all or part of the bottom wound-facing side of the body portion 221 of the "triangular gauze" adhesive bandage 220. The gauze pad 222 may or may not be affixed to the body portion 221 of the "triangular gauze" adhesive bandage 220 via the same adhesive as that which is used to affix the "triangular gauze" adhesive bandage 220 to a patient.

FIGS. 23(a)-23(g) are, respectively, a bottom wound-facing view, a top non-wound facing view, four side views and one perspective view of another exemplary embodiment of a "triangular gauze" adhesive bandage 230 according to the present invention. The "triangular gauze" adhesive bandage 230 has a body portion 231 in a triangular shape, preferably with rounded corners, and may be made of any suitable material, preferably a stretchable and breathable material, which is known in the art to be used for adhesive bandages. The gauze pad 232 is a triangular shape, preferably an equilateral triangular shape, but the gauze pad 232 may alternatively be configured as an isosceles, right or other triangular shape and may have rounded or flattened corners. The gauze pad 232 may be positioned so as to have the same center point as the body portion 231, with each of the corners of the gauze pad 232 extending to the sides of body portion 231. Alternatively, the gauze pad 232 may be sized so that the corners of the gauze pad 232 do not reach the sides of the body portion 231. The gauze pad 232 may be sized and positioned so as to substantially define three equal quadrants on the wound facing side of the body portion 231. The bottom wound-facing side of the body portion 231 of the "triangular gauze" adhesive bandage 230 may have adhesive as those used for bandages in the art. The adhesive may be applied to all or part of the bottom wound-facing side of the body portion 231 of the "triangular gauze" adhesive bandage 230. The gauze pad 232 may or may not be affixed to the body portion 231 of the "triangular gauze" adhesive bandage 230 via the same adhesive as that which is used to affix the "triangular gauze" adhesive bandage 230 to a patient.

Figure 24A:
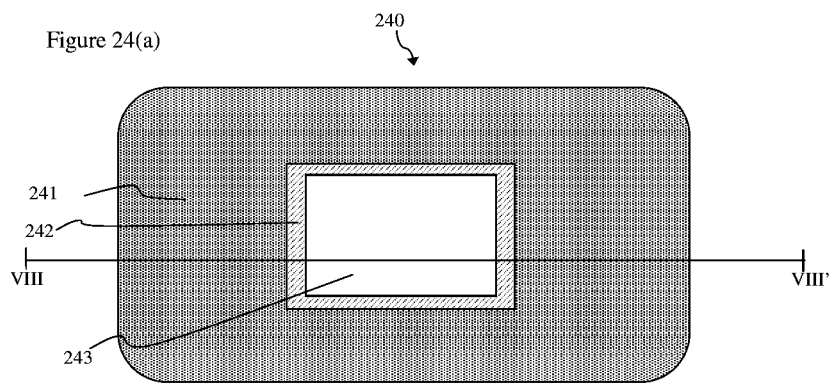
FIG. 24(a) shows a top non-wound-facing view of an exemplary embodiment of a bandage with a wound portal according to the present invention.
Figure 24B:
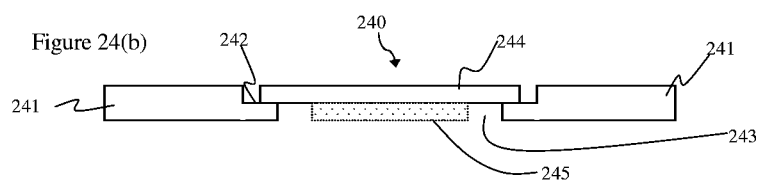
FIG. 24(b) is a side cross-sectional view of the bandage illustrated in FIG. 24(a) taken along line VIII-VIII'.

FIGS. 24(a) and 24(b) are, respectively, a top non-wound facing view and a cross-sectional side view taken along the line VIII-VIII' of an exemplary embodiment of a bandage 240 with a wound portal according to the present invention. The bandage 240 has a body portion 241 with an aperture 243. The aperture 243 is preferably sized to be greater than the size of a wound it is intended to bandage. The body portion 241 preferably has a shelf 242 surrounding the aperture 243. A cover 244, which is only shown in FIG. 24(b), is sized to substantially fill the aperture 243 and to extend at least partially onto the shelf 242. Preferably, the thickness of the cover 244 and the shelf 242 together should be approximately equal to or less than the thickness of the body portion 241 immediately surrounding the shelf 242 so that the top of the cover 244 will be flush or lower than portions of the body portion 241 that surround the shelf 242 and the aperture 243. The cover 244 may be held in place via an adhesive suitable for bandages as is known in the art that is either applied to the shelf 242 or to the cover 244. The adhesive may be a reusable pressure sensitive adhesive such as that used in post-it notes. Alternatively, the cover 244 may be held in place by some other fastening system such as hook and loop.

A gauze pad 245 may be placed within the aperture 243 to cover a wound. The gauze pad 245 may be attached to the cover 244 via a reusable pressure sensitive adhesive such as that used in post-it notes or by some other fastening system such as hook and loop or by a more permanent form of fastening. Alternatively, the gauze pad 245 may not be attached to the cover 244 and may instead be held in place by the cover 244 and/or by the sides of the aperture 243 without use of adhesive.

Figure 24C:
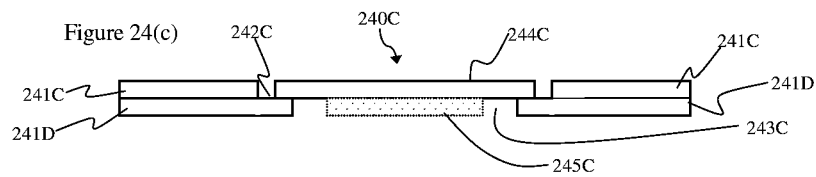
FIG. 24(c) is a side cross-sectional view of an alternative configuration of the exemplary embodiment of the bandage with a wound portal illustrated in FIG. 24(a)

In another alternative configuration of the wound portal as shown in FIG. 24(c), a bandage 240C has a body portion comprised a top layer 241C and a bottom layer 241D. The top and bottom layers 241C, 241D are affixed to each other and are sized such that the bottom layer 241D forms a shelf 242C around an aperture 243C. Similar to the cross-section shown in FIG. 24(b), a cover 244C is sized to substantially cover the aperture 243C and preferably extends at least partially onto the shelf 242C. Similar to the cross-section in FIG. 24(b), the gauze pad 245C that is within the aperture 243C may be attached to the cover 244C. Alternatively, the gauze pad 245C may not be attached to the cover 244C and may instead be held in place by the cover 244C and/or by the sides of the aperture 243C without use of adhesive.

Figure 24D:
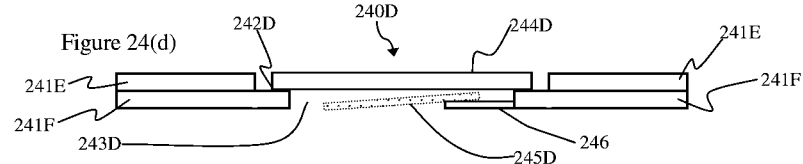
FIG. 24(d) is a side cross-sectional view of an alternative configuration of the exemplary embodiment of the bandage with a wound portal illustrated in FIG. 24(a)

In a further alternative configuration of the wound portal as shown in FIG. 24(d), similar to the configuration of the bandage 240C shown in FIG. 24(c), the bandage 240D has a body portion comprising a top layer 241E and a bottom layer 241F. The top and bottom layers 241E, 241F are affixed to each other and are sized such that the bottom layer 241F forms a shelf 242D around an aperture 243D. A cover 244D is sized to substantially cover the aperture 243D and preferably extends at least partially onto the shelf 242D. A gauze port 246 may be a separate piece of material attached to the bottom layer 241F or may be an integral protuberance of the bottom layer 241F. The gauze port 246 has an area either on a top non-wound facing side and/or a bottom wound facing side where a gauze pad 245D may be attached or removably attached. The top non-wound facing side of the gauze port 246 is the side facing the cover 244D where the gauze pad 245D is attached in FIG. 24(d). The bottom wound facing side of the gauze port 246 is the opposing side. The gauze port 246 may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze port 246 may be comprised of an adhesive that allows for the permanent attachment of the gauze pad 245D. The gauze port 246 may be used to attach different sized gauze pads 245D as well as to periodically replace the gauze pad 245D in the bandage 240D shown in this embodiment. The gauze port 246 may be sized and or configured so as to attach to all, a substantial portion, or a small portion such as one side of the gauze pad 245D.

Figure 24E:
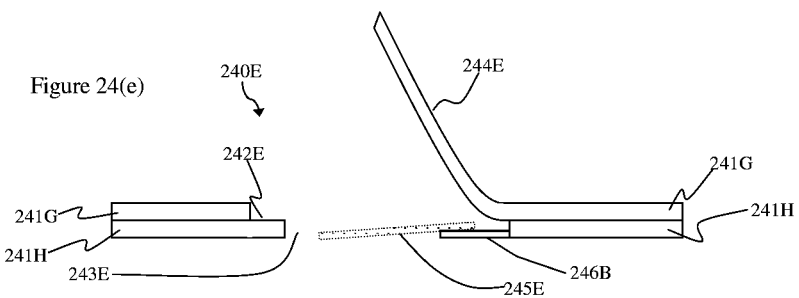
FIG. 24(e) is a side cross-sectional view of another exemplary embodiment of a bandage with a wound portal according to the present invention with a flap in an open position.
Figure 24F:
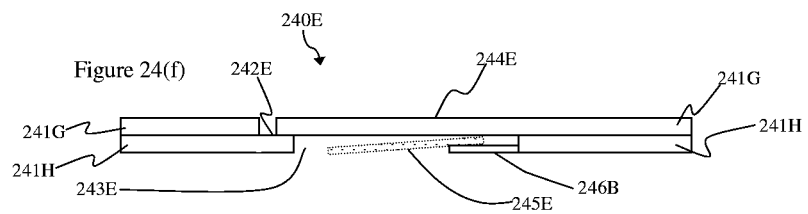
FIG. 24(f) is a side cross-sectional view of the exemplary embodiment of a bandage with a wound portal illustrated in FIG. 24(e) with the flap in a closed position.

In a further alternative configuration of the wound portal as shown in FIGS. 24(e) and 24(f), similar to the configuration of the bandage 240C shown in FIG. 24(c), the bandage 240E has a body portion comprising a top layer 241G and a bottom layer 241H. The top and bottom layers 241G, 241H are affixed to each other. An aperture 243E is formed in the bottom layer 241H and the top layer 241G has a flap 244E that covers the aperture 243E in the bottom layer 241H. The flap 244E preferably extends at least partially onto a shelf 242E that is formed at least partially around the aperture 243E. The flap 244E is sized so as to allow for the placement of a gauze pad 245E in the aperture 243E. In FIG. 24(e), the flap 244E is shown in an open position so as to access the gauze pad 245E, and in FIG. 24(f), the flap 244E is shown in a closed position. A gauze port 246B may be a separate piece of material attached to the bottom layer 241H or may be an integral protuberance of the bottom layer 241H. The gauze port 246B has an area either on a top non-wound facing side and/or a bottom wound facing side where a gauze pad 245E may be attached or removably attached. The top non-wound facing side of the gauze port 246B is the side facing the cover 244E where the gauze pad 245E is attached in FIGS. 24(e) and 24(f). The bottom wound facing side of the gauze port 246B is the opposing side. The gauze port 246B may be comprised of non-stretchable material and may have a surface that is configured for repeated removal and attachment of gauze by having either a hook or loop fastening surface of a hook and loop type fastener or a surface that provides a good bond with a re-stickable adhesive such as that found in Post-it® notes. Alternatively, the surface of the gauze port 246B may be comprised of an adhesive that allows for the permanent attachment of the gauze pad 245E. The gauze port 246B may be used to attach different sized gauze pads 245E as well as to periodically replace the gauze pad 245E in the bandage 240E shown in this embodiment. The gauze port 246B may be sized and or configured so as to attach to all, a substantial portion, or a small portion such as one side of the gauze pad 245E. Alternatively, instead of the gauze pad 245E attaching to the gauze port 246B, the gauze pad 245E may be unattached and held in place by the cover 244E, or the gauze port 246B may be attached to the cover 244E.

Figure 25A:
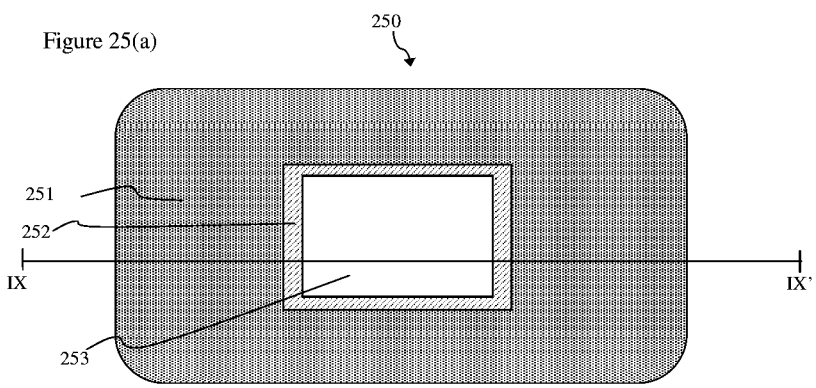
FIG. 25(a) shows a top non-wound-facing view of an exemplary embodiment of a bandage with a wound portal according to the present invention.
Figure 25B:
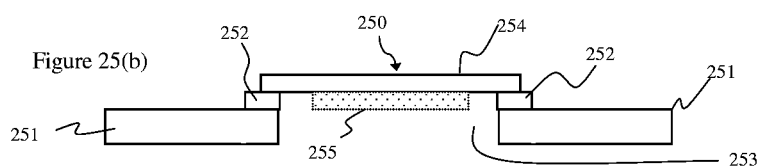
FIG. 25(b) is a side cross-sectional view of the bandage illustrated in FIG. 25(a) taken along line IX-IX'.

FIGS. 25(a) and 25(b) are, respectively, a top non-wound facing view and a cross-sectional side view taken along the line IX-IX' of another exemplary embodiment of a bandage 250 with a wound portal according to the present invention. The bandage 250 has a body portion 251 with an aperture 253. The aperture 253 is preferably sized to be greater than the size of a wound it is intended to bandage. Affixed to the body portion 251 around the perimeter of the aperture 253 is a flexible, yet non-stretchable or substantially non-stretchable rim 252, which may be made of a material such as silicone rubber. The rim 252 may be affixed to the non-wound facing side of the body portion 251, as shown in FIG. 25(b), or on the edges of the body portion 251 that surround and form the walls of the aperture 253 (not shown). The rim 252 is sized and configured so as to allow for removable attachment of a cover 254. The cover 254, which is only shown in FIG. 25(b), is sized to extend at least partially onto the rim 252 so as to close the aperture 253. A gauze pad 255 may be permanently or removably attached to the bottom wound-facing side of the cover 254. Alternatively, the gauze pad 255 may not be attached to the cover 254 and may instead be held in place by the cover 254 and/or by the sides of the aperture 253 without use of adhesive. The cover 254 may be held in place via an adhesive suitable for bandages as is known in the art that is either applied to the rim 252 or to the cover 254. The adhesive may be a reusable pressure sensitive adhesive such as that used in Post-it® notes. Alternatively, the cover 254 may be held in place by some other fastening system such as hook and loop.

Figure 26A:
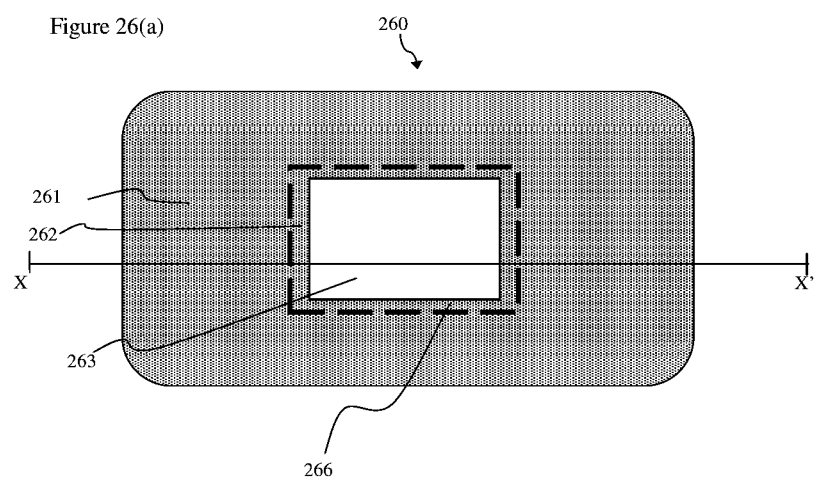
FIG. 26(a) shows a top non-wound-facing view of an exemplary embodiment of a bandage with a wound portal according to the present invention.
Figure 26B:
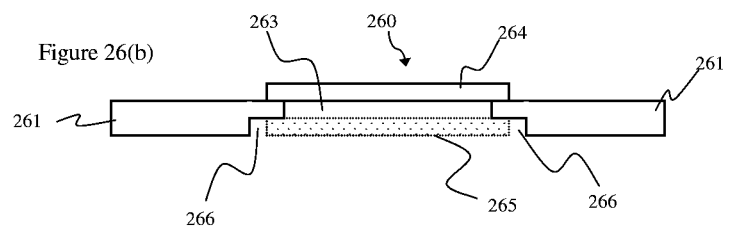
FIG. 26(b) is a side cross-sectional view of the bandage illustrated in FIG. 26(a) taken along line X-X'.

FIGS. 26(a) and 26(b) are, respectively, a top non-wound facing view and a cross-sectional side view taken along the line X-X' of another exemplary embodiment of a bandage 260 with a wound portal according to the present invention. The bandage 260 has a body portion 261 with an aperture 263. The aperture 263 is preferably sized to be greater than the size of a wound it is intended to bandage. The body portion 261 has a recess 266 in a bottom portion around the aperture 263. Although the recess 266 is not visible from the top non-wound facing view of the bandage 260, the recess 266 is indicated by a dashed line. The cover 264, shown only in FIG. 26(b) affixes to the top non-wound-facing surface of the body portion 261. As shown in FIG. 26(b), the gauze 265 that is within the aperture 263 is not attached to the cover 264 and is instead held in place by a protuberance from the top portion of the body portion 261 formed above the recess 266 around the aperture 263. However, as in previous embodiments of the bandages with a wound portal, the gauze 265 may be attached in some manner similar to that discussed by the gauze 255.

Figure 27A:
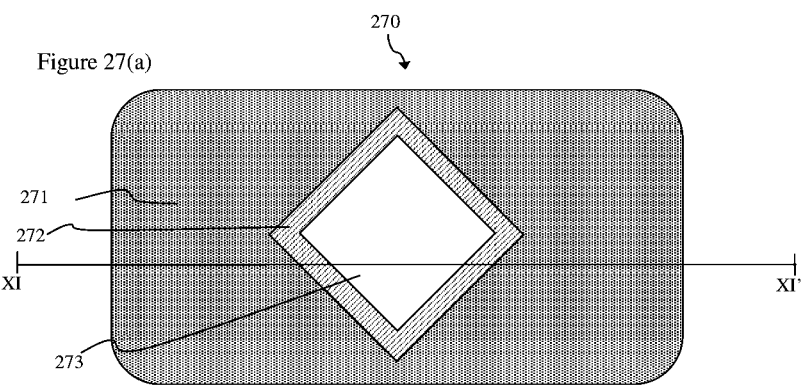
FIG. 27(a) shows a top non-wound-facing view of an exemplary embodiment of a "diamond gauze" bandage with a wound portal according to the present invention.
Figure 27B:
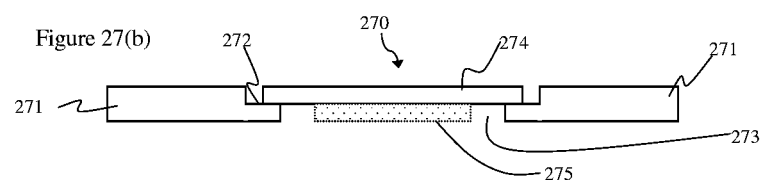
FIG. 27(b) is a side cross-sectional view of the "diamond gauze" bandage illustrated in FIG. 27(a) taken along line XI-XI'.

FIGS. 27(a) and 27(b) are, respectively, a top non-wound facing view and a cross-sectional side view taken along the line XI-XI' of an exemplary embodiment of a bandage 270 with a wound portal with a "diamond guaze" configuration according to the present invention. It should be noted that the bandage 270 incorporates a "diamond gauze" configuration, comparable to that of the bandage 140, with the wound portal configuration of the bandage 240. However, other wound portal configurations such as those in the bandages 240C, 240D, 240E may, alternatively, be used in the bandage 270. Moreover, all "diamond gauze" and "triangle gauze" bandage configurations may incorporate wound portals with configurations such as those shown in the bandages 240, 240C, 240D, and 240E.

The bandage 270 has a body portion 271 with an aperture 273 that is a square shape. Alternatively, the aperture 273 may be configured in the shape of a diamond or rhombus. Corners of the aperture 273 are offset from the corners of the body portion 271 such that the sides of the aperture 273 are not parallel to the sides of the body portion 271. The aperture 273 may have the same center point as the body portion 271, and/or each of the corners of the aperture 273 may be oriented toward a mid-point of one of the sides of body portion 271.

A bottom wound-facing side of the body portion 271 may have adhesive such as those used for bandages in the art. The aperture 273 is preferably sized to be greater than the size of a wound it is intended to bandage. The body portion 271 preferably has a shelf 272 surrounding the aperture 273.

A cover 274, which is only shown in FIG. 27(b), is sized to substantially fill the aperture 273 and to extend at least partially onto the shelf 272. Preferably, the thickness of the cover 274 and the shelf 272 together should be approximately equal to or less than the thickness of the body portion 271 immediately surrounding the shelf 272 so that the top of the cover 274 will be flush or lower than portions of the body portion 271 that surround the shelf 272 and the aperture 273. The cover 274 may be held in place via an adhesive suitable for bandages as is known in the art that is either applied to the shelf 272 or to the cover 274. The adhesive may be a reusable pressure sensitive adhesive such as that used in Post-it® notes. Alternatively, the cover 274 may be held in place by some other fastening system such as hook and loop.

A gauze pad 275 may be placed within the aperture 273 to cover a wound. The gauze pad 275 may be attached to the cover 274 via a reusable pressure sensitive adhesive such as that used in Post-it® notes or by some other fastening system such as a hook and loop or by a more permanent form of fastening. Alternatively, the gauze pad 275 may not be attached to the cover 274 and may instead be held in place by the cover 274 and/or by the sides of the aperture 273 without use of adhesive.

Figure 28:
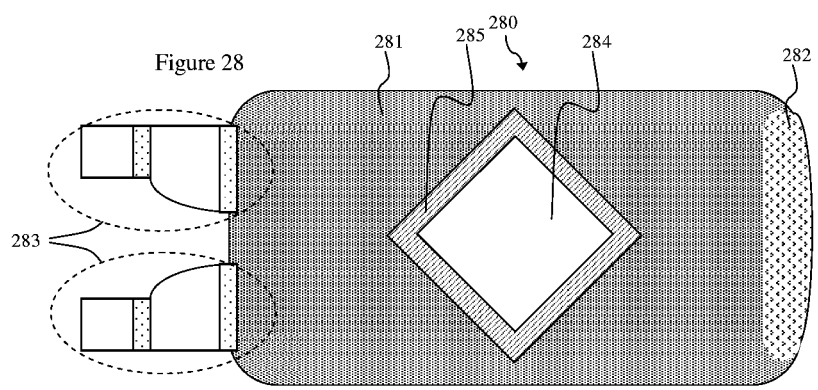
FIG. 28 shows a top non-wound-facing view of an exemplary embodiment of a bandage/wound protector with a wound portal and a "diamond gauze" configuration according to the present invention.

FIG. 28 is a top non-wound facing view of an exemplary embodiment of a bandage 280, according to the present invention. The bandage 280 incorporates the wound portal configuration of the bandage 270 into the bandage/wound protector 60. In other words, the bandage 280 has a body portion 281 that is configured as a wrap, first-catch fastening surface 282 and two fastening straps 283 that are configured in the same manner as in the bandage/wound protector 60 with an aperture 284, shelf 285, cover (not shown in figure) and gauze pad (not shown in figure) configured in the same manner as in the bandage 270. All of the exemplary embodiments of wound portal bandage configurations discussed above such as those shown in the exemplary embodiments of bandages shown in FIGS. 24-27 may be incorporated into any of the bandage/wound protectors 20, 30, 40, 50, 60, 70, 80, 100 and 110 discussed above and/or with any of the "diamond gauze" and "triangular gauze" bandages 120, 130, 140, 150, 160, 170, 180, 190, 200, 210, 220, and 230. Moreover, any of the bandage/wound protectors 20, 30, 40, 50, 60, 70, 80, 100 and 110 discussed above may be combined with any of the "diamond gauze" and "triangular gauze" bandages 120, 130, 140, 150, 160, 170, 180, 190, 200, 210, 220, and 230 without a wound portal configuration.

Figure 29A:
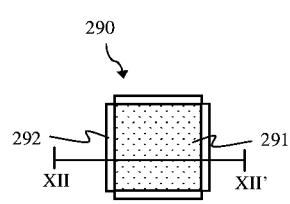
FIG. 29(a) is a top view of an exemplary embodiment of a frictional gauze pad according to the present invention.
Figure 29B:
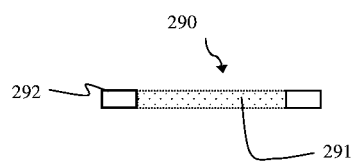
FIG. 29(b) is a side cross-sectional view of the frictional gauze pad illustrated in FIG. 29(a) taken along line XII-XII'.

FIGS. 29(a) and 29(b) are, respectively, a top view and a side cross-sectional view taken along line XII-XII' of an exemplary embodiment of a frictional gauze pad 290 according to the present invention. The frictional gauze pad 290 has a pad portion 291 and a frame 292. The pad portion 291 may be comprised of materials similar to that of the frictional gauze pads discussed above. The frame 292 is attached to and extends from the edge of the pad portion 291. The frame 292 may be comprised of a self-adherent material or a rubberized or tacky material and may have a similar configuration as the strip 62 in FIG. 6(a) above. The frictional gauze pad 290 can be used instead of a gauze port or similar method of securing the gauze in place by providing a frictional or similar resistance between the frame 292 of the frictional gauze pad 290 and a bandage and/or a frictional or similar resistance between the frictional gauze pad 290 and the area surrounding the wound. Thus, for example, in the bandage/wound protector 60, in lieu of providing a gauze port 62A, one may use the frictional gauze pad 290. In addition, the bandage/wound protector 60 may be further configured to include a corresponding self-adherent material or a rubberized or tacky surface on the wound facing side of the body portion 61 to further enhance the frictional or similar resistance between the wound/bandage protector 60 and the frictional gauze pad 290. One skilled in the art would understand that this frictional gauze pad 290 may be applied to any and all of the bandages discussed above as well as to other bandages known in the art.

Figure 30A:
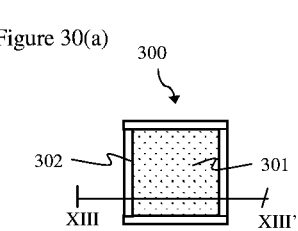
FIG. 30(a) is a top view of an exemplary embodiment of a frictional gauze pad according to the present invention.
Figure 30B:
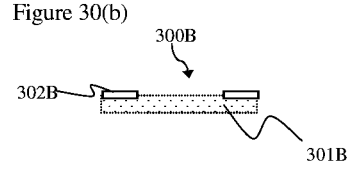
FIG. 30(b) is a first exemplary cross-sectional view of the frictional gauze pad illustrated in FIG. 30(a) taken along line XIII-XIII'.
Figure 30D:
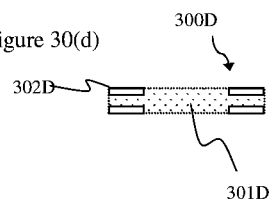
FIG. 30(d) is a third exemplary cross-sectional view of the frictional gauze pad illustrated in FIG. 30(a) taken along line XIII-XIII'.
Figure 30C:
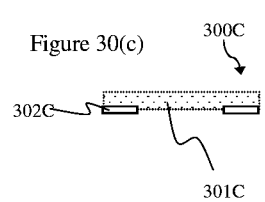
FIG. 30(c) is a second exemplary cross-sectional view of the frictional gauze pad illustrated in FIG. 30(a) taken along line XIII-XIII'.
Figure 30E:
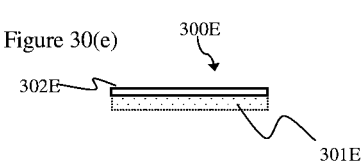
FIG. 30(e) is an alternative exemplary cross-sectional view of the frictional gauze pad according to the present invention.

FIGS. 30(a)-(e) show alternative exemplary embodiments of a frictional gauze pad according to the present invention. FIG. 30(a) may be a top view and/or a bottom view of a gauze pad 300 with a pad portion 301 and a frame 302. The pad portion 301 may be comprised of materials similar to that of the frictional gauze pad 290, discussed above. The frame 302 may be affixed to the top and/or bottom surface of the pad portion 301. Alternatively, the frame 302 may be attached to and extend from the edge of the pad portion 301. The frame 302 may be comprised of a self-adherent material or a rubberized or tacky material. FIG. 30(b) is a side cross-sectional view of one alternative embodiment of a frictional gauze pad 300B, with a frame 302B, that has the same configuration as the frame 302, attached to the top surface of a pad portion 301B of the frictional gauze pad 300B. FIG. 30(c) is a side cross-sectional view of another alternative embodiment of a frictional gauze pad 300C, with a frame 302C, that has the same configuration as the frame 302, attached to the bottom surface of a pad portion 301C of the frictional gauze pad 300C. FIG. 30(d) is a side cross-sectional view of another alternative embodiment of a frictional gauze pad 300D, with a frame 302D, that has the same configuration as the frame 302, attached to both the top surface and the bottom surface of a pad portion 301D of the frictional gauze pad 300D. FIG. 30(e) is a side cross-sectional view of another alternative embodiment of a frictional gauze pad 300E in which a frame 302E is extended to cover the entire top surface of a pad portion 301E. This embodiment may be combined with the frictional gauze pad 300C in which the frame 302C is attached to the bottom of the pad portion 301C.

The embodiments of the invention described herein are exemplary in nature, and therefore, the spirit and the scope of the invention are by no means restricted to what is described above or intended to represent every possible embodiment of the invention. For example, when hook or loop of a hook and loop type fastener is mentioned, the hook portion could be the loop portion and the loop portion could be the hook portion, or it could be a different type of fastening system altogether such as reusable adhesive with a surface that can adhere well to a reusable adhesive or magnetic fasteners, or a self adhering material surfaces, snaps, buttons. Moreover, where reusable adhesive is mentioned, could also be any other form of fastening, or releasable fastening, and in cases where permanent fastening is a possibility, use of other methods of attachment such as heat and punch or sewing may also be used. A gauze pad does not need to be square or rectangular it may be any shape that is sufficient to treat a particular wound. The wound/bandage protectors may or may not be configured with a first catch tab and the tab may or may not be configured with a fastener or fastening surface Likewise, structural limitations discussed by one exemplary embodiment of a wound/bandage protector or sock/mitten or bandage or adhesive bandage may be applied to other exemplary embodiments of the wound/bandage protector or sock/mitten or bandage or adhesive bandage.

What is claimed is:
1. A wound/bandage protector comprising:
 a. a body portion configured as a wrap having a first end, a second end, a wound facing side and a non-wound facing side;
 b. a first-catch fastening surface on an end region of the non-wound facing side of the body portion configured so as to be capable of fastening with at least a portion of the wound facing side of the body portion, the end region being proximal to the first end of the body portion;
 c. a first fastening strap extending from the second end of the body portion, at least a portion of a wound facing side surface of the first fastening strap configured so as to be capable of fastening with at least a portion of the non-wound facing side of the body portion or a non-wound facing side of the first fastening strap; and d. a cover, wherein the body portion contains an aperture, and the cover and the aperture are sized so as to allow the cover to completely close the aperture.

2. The wound/bandage protector of claim 1, wherein the body portion is configured with a shelf surrounding the aperture, and the cover is sized so as to close the aperture and to extend at least partially onto the shelf.

3. The wound/bandage protector of claim 1, further comprising a non-stretchable or substantially non-stretchable rim provided on the non-wound-facing side surface of the body portion surrounding the aperture, wherein the surface of the rim is sized and configured so as to allow for removable attachment of the cover.

4. A wound/bandage protector comprising:
   a. a body portion configured as a wrap having a first end, a second end, a wound facing side and a non-wound facing side;
   b. a first-catch fastening surface on an end region of the non-wound facing side of the body portion configured so as to be capable of fastening with at least a portion of the wound facing side of the body portion, the end region being proximal to the first end of the body portion; and
   c. a first fastening strap extending from the second end of the body portion, at least a portion of a wound facing side surface of the first fastening strap configured so as to be capable of fastening with at least a portion of the non-wound facing side of the body portion or a non-wound facing side of the first fastening strap;
   wherein the body portion is configured to be stretchable in a lengthwise direction, the lengthwise direction being defined by the first end of the body portion and the second end of the body portion and the first fastening strap is comprised of a first strap part that is stretchable, and a second strap part that includes the portion of the first fastening strap capable of fastening with at least a portion of the non-wound facing side of the body portion or the non-wound facing side of the first fastening strap, wherein an elastic modulus of the first strap part is greater than an elastic modulus of the body portion, and wherein the wound-facing side of the body portion is configured with a tacky surface.

5. A wound/bandage protector comprising:
   a. a body comprised of stretchable material configured as a sock/mitten having a first end that is open, a second end that is closed, an internal wound facing side and an external non-wound facing side;
   b. a first strap part connected to the body comprised of stretchable material;
   c. a second strap part connected to the first strap part, at least a portion of a wound-facing side of the second strap part configured so as to be capable of fastening with at least a portion of the external non-wound facing side of the body, at least a portion of a non-wound facing side of the first strap part, and at least a portion of a non-wound facing side of the second strap part;
   d. a fastening strap comprised of the first strap part and the second strap part; and
   e. a sheath with a first open end, and a second closed end, the sheath sized and configured to fit over an entirety of the body, a slot or slit in the sheath sized and positioned so as to allow the fastening strap to fit therethrough, the fastening strap sized so as to be capable of extending around an outside of the sheath to secure both the body and the sheath to an appendage being bandaged by fastening the wound facing side of the second strap part to a non-wound facing side of the fastening strap.

6. The wound/bandage protector of claim 5, further comprising:
   a. a third strap part that is configured as a dead zone connecting the first strap part to the external non-wound facing side of the body; and
   b. a fourth strap part that is configured as a dead zone connecting the first strap part and the second strap part, wherein the fastening strap further comprises the third strap part and the fourth strap part.

7. The wound/bandage protector of claim 6, wherein the third strap part and the fourth strap part have a rubberized or tacky surface exposed on at least the wound facing side of the fastening strap.

8. The wound/bandage protector of claim 5, wherein the body has a panel configured to have little or no stretch.

9. A wound/bandage protector comprising:
   a. a body portion configured as a wrap having a first end, a second end, a wound facing side and a non-wound facing side;
   b. a first-catch fastening surface on an end region of the non-wound facing side of the body portion configured so as to be capable of fastening with at least a portion of the wound facing side of the body portion, the end region being proximal to the first end of the body portion;
   c. a first fastening strap extending from the second end of the body portion, at least a portion of a wound facing side surface of the first fastening strap configured so as to be capable of fastening with at least a portion of the non-wound facing side of the body portion or a non-wound facing side of the first fastening strap; and
   d. a gauze pad adjacent but unattached to the wound facing side of the body portion, the gauze pad having a rubberized or tacky frame on a wound-facing and/or non-wound-facing side of the gauze pad.

10. A wound/bandage protector comprising:
    a. a body portion configured as a wrap having a first end, a second end, a wound facing side and a non-wound facing side;
    b. a first-catch fastening surface on an end region of the non-wound facing side of the body portion, the end region being proximal to the first end of the body portion;
    c. a first fastening strap extending from the second end of the body portion, at least a portion of a wound facing side surface of the first fastening strap configured so as to be capable of fastening with at least a portion of the non-wound facing side of the body portion or a non-wound facing side of the first fastening strap;
    d. a gauze port on the wound facing side of the body portion proximal to the first end of the body portion, the gauze port being configured to attach to only a small portion of a gauze pad proximal to one side of the gauze pad and to allow repeated removable attachment of the gauze pad; and
    e. a strip provided on the body portion between the gauze port and the first end of the body portion, the strip comprised of a rubberized material exposed on at least the wound facing side of the body portion, wherein
       i. the body portion is configured to be stretchable in a lengthwise direction, the lengthwise direction being defined by the first end of the body portion and the second end of the body portion,
       ii. the first fastening strap is comprised of a first strap part that is stretchable, and a second strap part that includes the portion of the first fastening strap capable of fastening with at least a portion of the non-wound facing side of the body portion or the non-wound facing side of the first fastening strap, and iii. an elastic modulus of the first strap part is greater than an elastic modulus of the body portion.

* * * * *